US011406524B2

(12) United States Patent
Ponsi et al.

(10) Patent No.: US 11,406,524 B2
(45) Date of Patent: Aug. 9, 2022

(54) CUSHIONED SUPPORT SYSTEM FOR HEEL ULCER PREVENTION

(71) Applicant: SAGE PRODUCTS, LLC, Cary, IL (US)

(72) Inventors: Larry Ponsi, Cary, IL (US); Curtis L. Hollabaugh, Cary, IL (US); Hester C. Fletcher, Louisa, VA (US); Craig S. Golden, Cary, IL (US)

(73) Assignee: SAGE PRODUCTS, LLC, Cary, IL (US)

( * ) Notice: Subject to any disclaimer, the term of this patent is extended or adjusted under 35 U.S.C. 154(b) by 625 days.

(21) Appl. No.: 15/829,657

(22) Filed: Dec. 1, 2017

(65) Prior Publication Data

US 2018/0153729 A1 Jun. 7, 2018

Related U.S. Application Data

(60) Provisional application No. 62/429,429, filed on Dec. 2, 2016, provisional application No. 62/525,516, filed on Jun. 27, 2017.

(51) Int. Cl.
*A61F 5/00* (2006.01)
*A61F 5/34* (2006.01)
*A61G 7/057* (2006.01)
*A61G 7/075* (2006.01)
*A44B 11/25* (2006.01)
*A61G 13/12* (2006.01)

(52) U.S. Cl.
CPC .......... *A61F 5/34* (2013.01); *A44B 11/2592* (2013.01); *A61G 7/057* (2013.01); *A61G 7/0755* (2013.01); *A61G 13/125* (2013.01); *A61G 13/1245* (2013.01); *A61G 13/126* (2013.01)

(58) Field of Classification Search
CPC ........ A61F 5/34; A61F 5/0111; A61F 5/0127; A61F 5/05841; A61F 5/0585; A61F 5/3761; A61F 5/3769; A61F 13/064; A61F 13/069; A61F 13/06; A44B 11/2592; A61G 7/0755; A61G 13/1245; A61G 13/125; A61G 13/126; A61G 7/05723; A61G 7/057; A61G 2200/32; A61G 2200/56
USPC .................................. 128/882, 889, 892–893
See application file for complete search history.

(56) References Cited

U.S. PATENT DOCUMENTS 3,535,718 A * 10/1970 Murcott ................ A61F 5/3761
128/878
4,422,455 A * 12/1983 Olsen .................... A61F 5/3761
128/878
4,616,639 A 10/1986 Huber
5,085,214 A * 2/1992 Barrett ..................... A61F 5/01
128/882

(Continued)

OTHER PUBLICATIONS

International Search Report and Written Opinion for International Application No. PCT/US2017/064300, dated Mar. 26, 2018, 12 pages.

*Primary Examiner* — Camtu T Nguyen
(74) *Attorney, Agent, or Firm* — Foley & Lardner LLP

(57) ABSTRACT

A cushioned support device includes a pad for supporting a portion of a patient's leg, a securing system coupled to the pad and configured to secure the portion of the patient's leg to the pad, and a connecting member coupled to the pad and configured to couple the cushioned support device to a second cushioned support device.

19 Claims, 15 Drawing Sheets

(56) References Cited

U.S. PATENT DOCUMENTS

| | | | | |
|---|---|---|---|---|
| 5,362,305 A | * | 11/1994 | Varn | A61F 5/0193 |
| | | | | 128/882 |
| 6,260,221 B1 | * | 7/2001 | Grabell | A47C 20/021 |
| | | | | 128/882 |
| D542,921 S | | 5/2007 | Ponsi et al. | |
| 7,798,984 B2 | * | 9/2010 | Ponsi | A61F 5/0111 |
| | | | | 602/61 |
| 8,136,186 B1 | * | 3/2012 | Leach | A47C 27/086 |
| | | | | 5/631 |
| 8,152,749 B2 | | 4/2012 | Ponsi et al. | |
| 8,156,941 B1 | | 4/2012 | Simms | |
| 8,628,487 B2 | | 1/2014 | Ponsi et al. | |
| 8,894,598 B2 | | 11/2014 | Ponsi et al. | |
| 2003/0159699 A1 | | 8/2003 | Anderson et al. | |
| 2005/0060808 A1 | | 3/2005 | Shaw | |
| 2017/0304104 A1 | * | 10/2017 | Janning | A61F 5/0104 |

\* cited by examiner

CUSHIONED SUPPORT SYSTEM FOR HEEL ULCER PREVENTION

CROSS-REFERENCE TO RELATED PATENT APPLICATIONS

This application claims the benefit of and priority to U.S. Provisional Patent Application No. 62/429,429, filed Dec. 2, 2016 and U.S. Provisional Patent Application No. 62/525,516, filed Jun. 27, 2017, each of which is hereby incorporated by reference in its entirety.

BACKGROUND

Cushioned calf supports have been developed for protecting the anatomy of a patient who is bedridden. The devices are configured to provide limb support and comfort, and in particular, to limit contact and pressure of a patient's heel resting on the bed, which may cause discomfort or injury (e.g., pressure ulcers) for a patient who must remain bedridden for an extended period of time.

The embodiments of the present disclosure seek to overcome drawbacks of existing devices, systems, and methods for protecting a patient's heel while bedridden, and to provide new features not heretofore available.

BRIEF DESCRIPTION OF THE DRAWINGS

To understand the present disclosure, it will now be described by way of example, with reference to the accompanying drawings in which.

DETAILED DESCRIPTION

A cushioned support device, such as a cushioned foot and/or calf support, may be used to support a bedridden a patient who may, for example, be unconscious or still. The cushioned support device includes multiple cushioned pads configured for positioning and supporting a foot and/or calf of a patient to minimize contact of the heel with a support surface. The disclosure is also directed to systems or kits including one or more of such devices. Various embodiments are described below.

Figure 1:
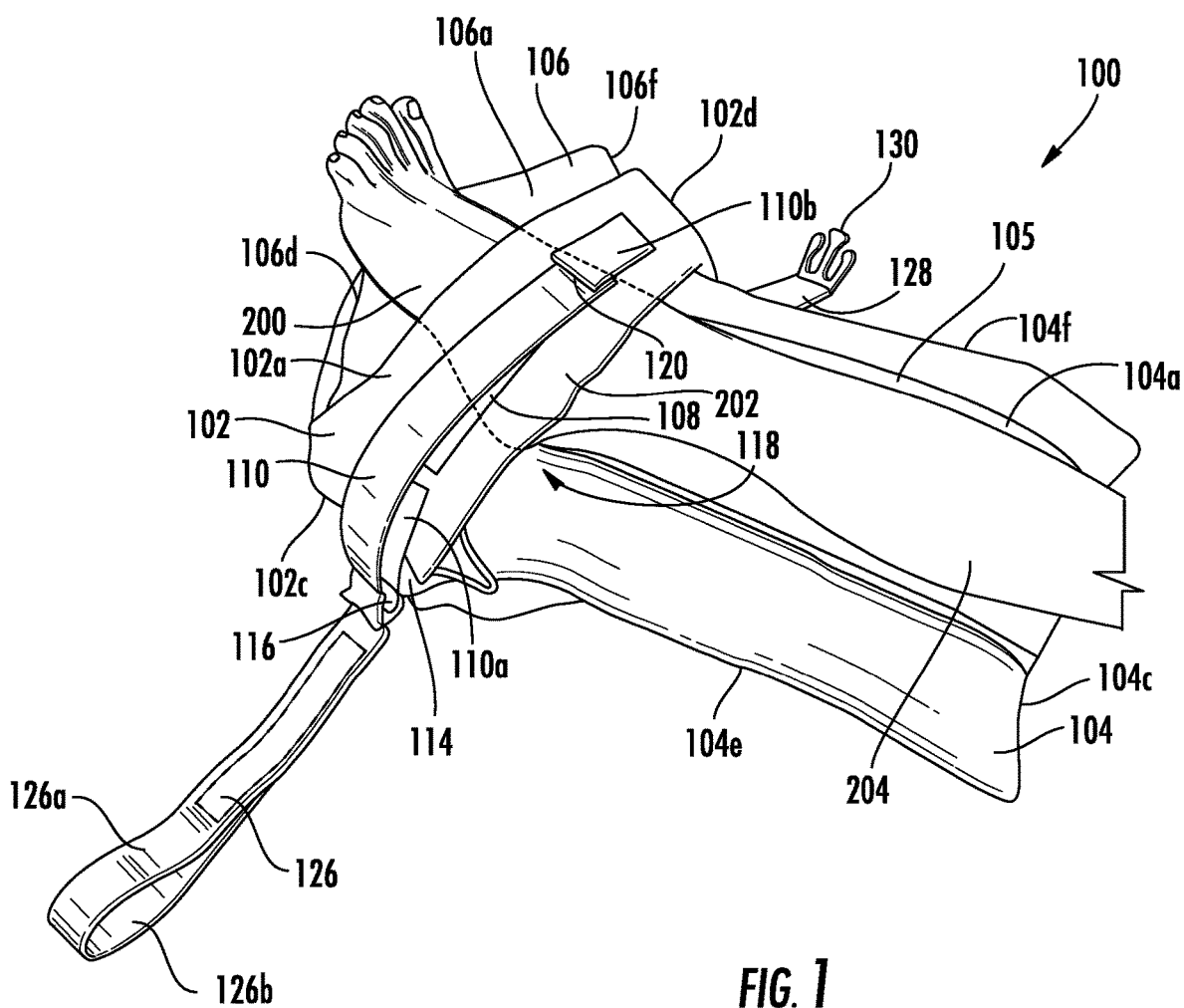
FIG. 1 is a top perspective view of a cushioned foot and calf support, according to an exemplary embodiment.

Referring to FIG. 1, a top perspective view of a cushioned foot and calf support 100 is shown, according to an exemplary embodiment. As shown in FIG. 1, the foot and calf support 100 is formed having a top pad 102, a calf pad 104, and a foot pad 106. The top pad 102, the calf pad 104, and the foot pad 106 are arranged such that the calf pad 104 is positioned adjacent to the foot pad 106 and that the top pad 102 is positioned extending across the top of the calf pad 104 and the foot pad 106. While the top pad 102, calf pad 104, and foot pad 106 are described herein as three separate pads, it should be understood that more or fewer pads may be used to form a foot and calf support. Further, while the top pad 102, calf pad 104, and foot pad 106 are each described as a single component, multiple pads may be used to form top pad 102, calf pad 104, and/or foot pad 106.

As shown in FIG. 1, outer edges of the top pad 102 form a rectangular or oblong shape, though in other embodiments, the outer edges of the top pad 102 may form a different shape such an elliptical shape, or the top pad 102 may be cylindrical. The top pad 102 includes a top surface 102a and a bottom surface 102b (shown in FIG. 3) opposite from the top surface 102a. The top pad 102 also includes a first end 102c and a second end 102d formed where the top surface 102a meets the bottom surface 102b, with the first end 102c opposite from the second end 102d. In some embodiments, the top pad 102 is created by stitching the top surface 102a and the bottom surface 102b together and inserting filling material (e.g., poly-fill) between the top surface 102a and the bottom surface 102b before the top surface 102a and the bottom surface 102b are completely stitched together. In other embodiments, the top surface 102a and the bottom surface 102b are formed as a single tube of material and are filled with filling material such that there is only stitching at the first end 102c or the second end 102d. In other embodiments the pads may be formed by some other method using another material such as molded or formed foam.

As further shown in FIG. 1, the top surface 102a includes a fastening strip 108. The fastening strip 108 may be constructed from a mechanical-based fastening product (e.g., part of a fabric hook-and-loop fastener), an adhesive product, and so on. Additionally, an adjustment strap 110 is secured to the top surface 102a (e.g., by stitching, by an adhesive, etc.) at a fastened end 110a. The adjustment strap 110 also includes a securing end 110b that is removably or temporarily coupled to the top surface 102a via the fastening strip 108. For example, the fastening strip 108 may be made of a fabric hook fastener material, and the bottom of the securing end 110b may include a fabric loop fastener material that removably attaches to the fastening strip 108 (e.g., shown as the darker section of the adjustment strap 110 in FIG. 3), or vice versa. In other embodiments, however, the adjustment strap 110 may be configured differently or may attach to the top pad 102 differently. As an example, the top pad 102 may not include the fastening strip 108. Instead, the securing end 110b may be removably or temporarily coupled to the fastened end 110a (e.g., because the securing end 110b includes a fabric hook fastener material and the fastened end 110a includes a fabric loop fastener material, or vice versa). The adjustment strap 110 is discussed in further detail below with reference to FIG. 3.

Outer edges of the calf pad 104 form a rectangular or oblong shape, though in other embodiments, the outer edges of the calf pad 104 may form a different shape such an elliptical shape, or the calf pad 104 may be cylindrical. As shown in FIG. 1, and in FIG. 2, which illustrates a bottom perspective view of the support 100, the calf pad 104 includes a top surface 104a and a bottom surface 104b opposite from the top surface 104a. The calf pad 104 further includes a proximal end 104c, a distal end 104d, a first side 104e, and a second side 104f formed where the top surface 104a meets the bottom surface 104b, with the proximal end 104c opposite the distal end 104d and the first side 104e opposite the second side 104f.

Figure 2:
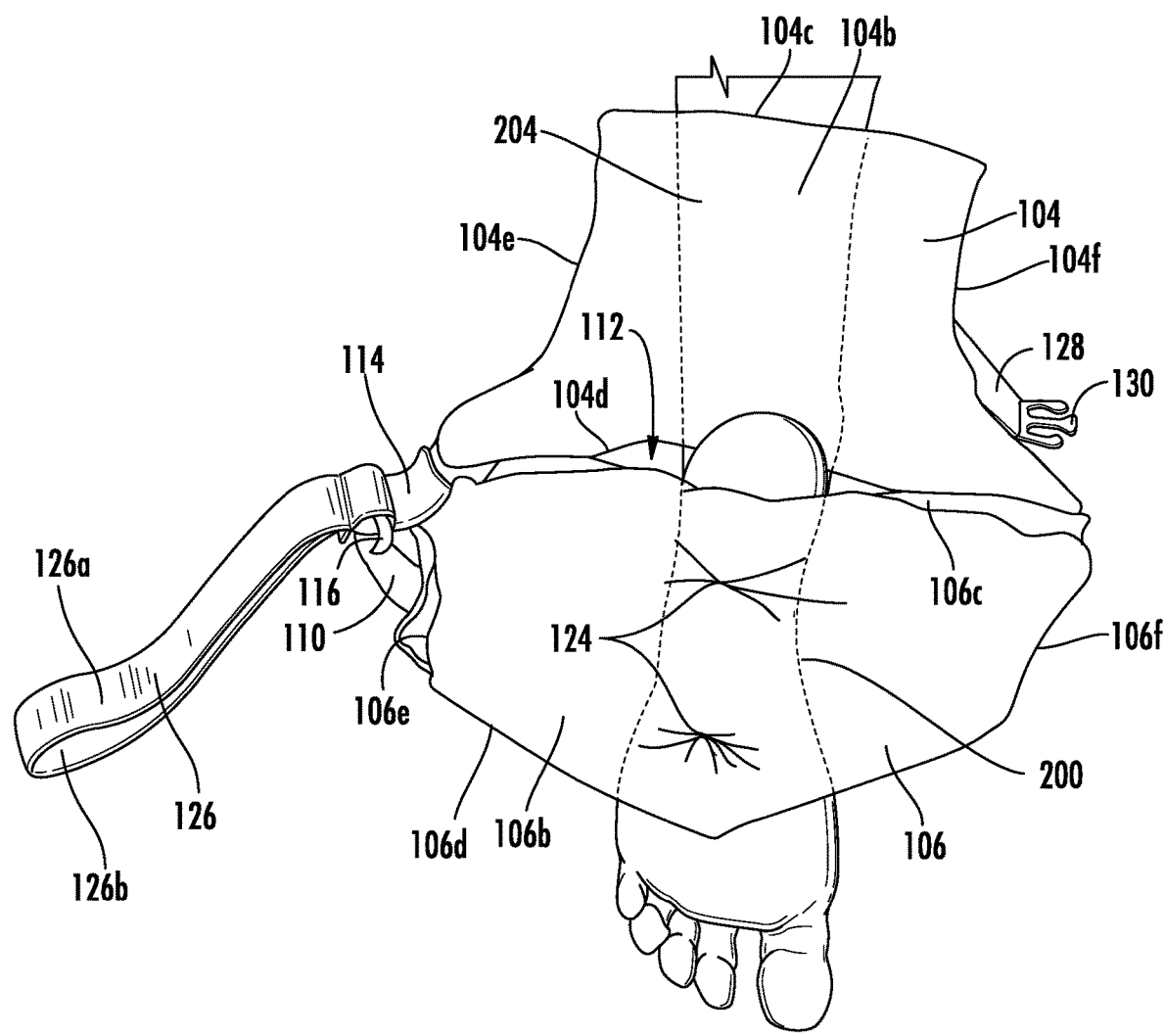
FIG. 2 is a bottom perspective view of the cushioned foot and calf support of FIG. 1, according to an exemplary embodiment.

As shown in FIGS. 1 and 2, outer edges of the foot pad 106 form a rectangular or oblong shape, though in other embodiments, the outer edges of the foot pad 106 may form a different shape such an elliptical shape, or the foot pad 106 may be cylindrical. The foot pad 106 includes a top surface 106a and a bottom surface 106b opposite from the top surface 106a. The foot pad 106 further includes a proximal end 106c, a distal end 106d, a first side 106e, and a second side 106f formed where the top surface 106a meets the bottom surface 106b. The proximal end 106c is opposite from the distal end 106d, and the first side 106e is opposite from the second side 106f. In various embodiments, the calf pad 104 and the foot pad 106 may be constructed similarly to the top pad 102, as described above.

Figure 5:
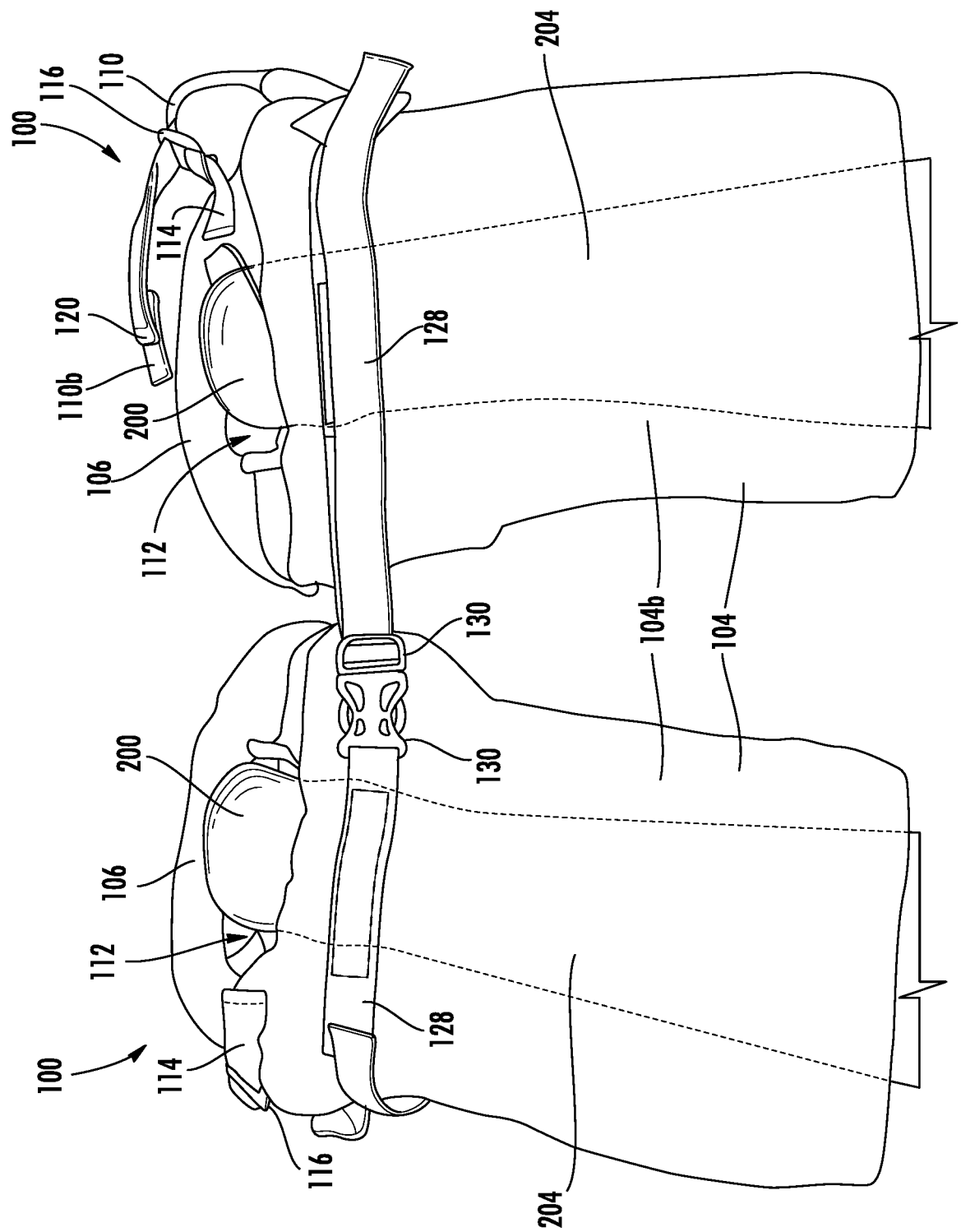
FIG. 5 is a bottom perspective view of two connected cushioned foot and calf supports, according to an exemplary embodiment.

As shown in FIG. 2, the calf pad 104 and the foot pad 106 are coupled together (e.g., sewn together, adhered together, etc.) at the distal end 104d of the calf pad 104 and the proximal end 106c of the foot pad 106. In some embodiments, as shown in FIG. 2, only the rightmost and leftmost portions of the distal end 104d and the proximal end 106c are coupled together such that a heel gap 112 exists between the calf pad 104 and the foot pad 106. The heel gap 112 provides a place to accommodate the heel of the patient's foot 200 (e.g., as shown in FIGS. 2 and 5). However, in other embodiments, the distal end 104d of the calf pad 104 and the proximal end 106c of the foot pad 106 may be completely coupled together such that no space exists between the distal end 104d and the proximal end 106c (e.g., the distal end 104d and the proximal end 106c may be completely sewn together).

Referring back to FIG. 1, the second end 102d of the top pad 102 is coupled (e.g., sewn to, adhered to, etc.) to the second side 104f of the calf pad 104 and/or the second side 106f of the foot pad 106. In one embodiment, the calf pad 104 includes a flap of material that folds around the second end 102d of the top pad 102 and is sewn onto the second end 102d of the top pad 102 to secure the top pad 102 to the calf pad 104. However, in other embodiments, the second end 102d of the top pad 102 may be coupled to the calf pad 104 or the foot pad 106 differently. For example, in various embodiments, the second end 102d of the top pad 102 may be sewn into the second side 106f of the foot pad 106 or sewn such that the second end 102d of the top pad 102 overlaps the junction between the calf pad 104 and the foot pad 106. Alternatively, a strip of fabric may connect the second end 102d of the top pad 102 to the second side 104f of the calf pad 104 or the second side 106f of the foot pad 106.

Figure 3:
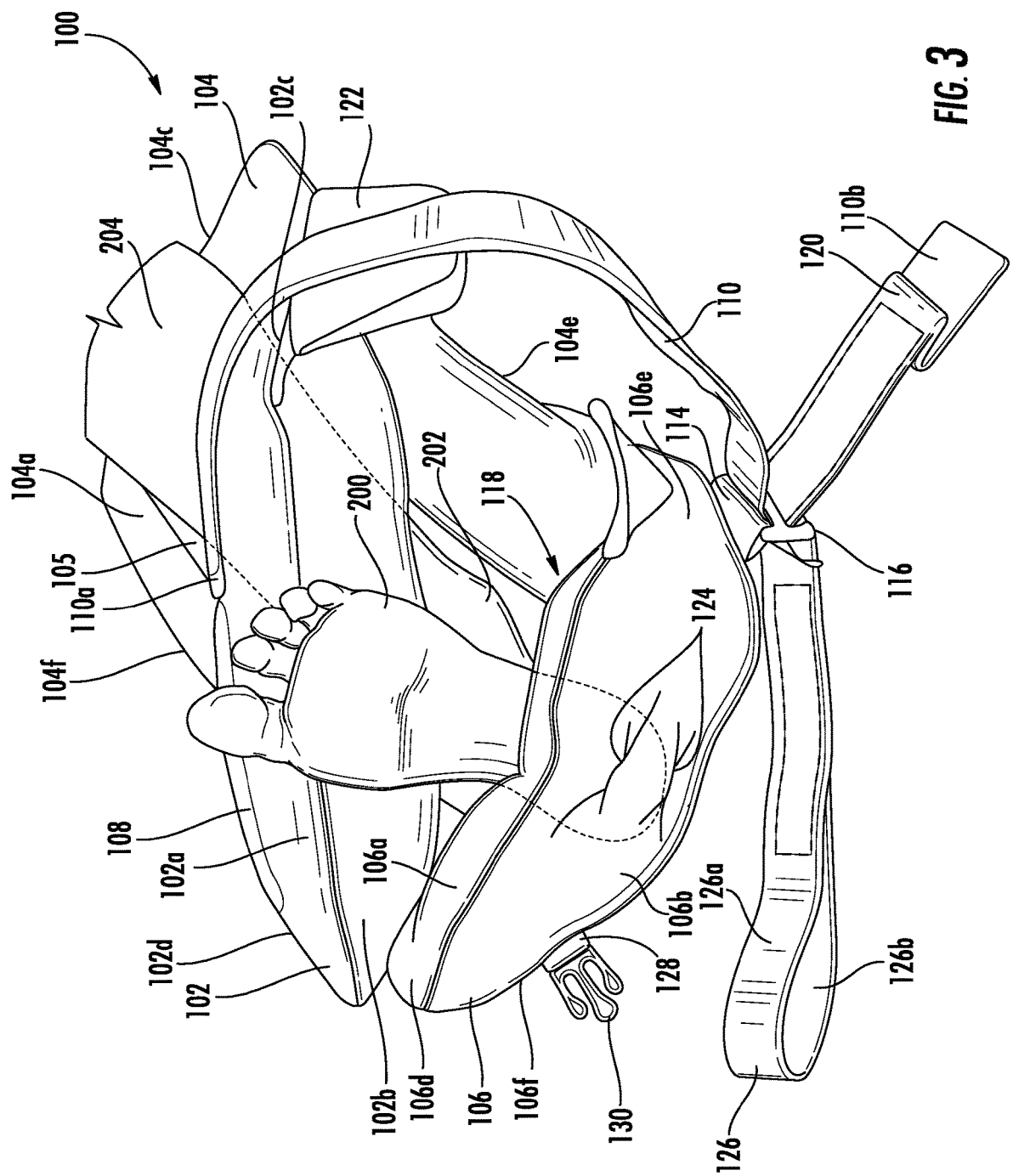
FIG. 3 is a second top perspective view of the cushioned foot and calf support of FIG. 1, according to an exemplary embodiment.

The first end 102c of the top pad 102 is coupled to the first side 104e of the calf pad 104 and/or the first side 106e of the foot pad 106 via the adjustment strap 110. As shown in FIG. 1 and more particularly in FIG. 2, the calf pad 104 includes a connecting strap 114 (e.g., near the junction between the distal end 104d of the calf pad 104 and the proximal end 106c of the foot pad 106). The connecting strap 114 holds an adjustment hook 116, which includes one or more rings that various straps can loop around or weave through. In various embodiments, the adjustment hook 116 may be a plastic ring, a metal ring, and so on. FIG. 3 illustrates a second top perspective view of the foot and calf support 100. As shown in FIG. 3, the connecting strap 114 forms a fabric loop that encircles a ring of the adjustment hook 116, thereby connecting the connecting strap 114 to the adjustment hook 116. However, in other embodiments, the connecting strap 114 may not include an adjustment hook and may, for example, instead be sewn around on itself to form a loop. As further shown in FIG. 3, the adjustment strap 110 is configured to thread through the adjustment hook 116, thereby connecting the top pad 102 to the calf pad 104 and the foot pad 106.

Referring to FIGS. 1 and 3, the top pad 102, calf pad 104, and foot pad 106 together form a space 118 in which a patient's foot 200 and ankle 202 may be placed. When placed in the space 118, the sole of the patient's foot 200 rests on the top surface 106a of the foot pad. In embodiments including the heel gap 112, the heel gap 112 accommodates the heel of the patient's foot 200, as shown in FIG. 2. Further, the patient's calf 204 rests on the top surface 104a of the calf pad 104. For example, the patient's calf 204 may rest on a different section of the calf pad 104, which may be made of a slightly deformable material (e.g., spandex) configured to conform to the patient's calf 204. The top pad 102 then rests on top of the patient's foot 200 and ankle 202 area to secure the patient's foot 200 into the foot and calf support 100. This configuration of the foot and calf support 100 is beneficial to patients because the foot pad 106 and the calf pad 104 cushion the patient's ankle 202, but the calf pad 104 prevents too much pressure from being placed on the patient's Achilles tendon by moving most of the pressure from the patient's Achilles tendon to the patient's calf 204. For example, the calf pad 104 is configured to allow a maximum of about 4,300 N/m$^2$ or about 32 mmHG of pressure on the heel or the Achilles tendon. Further, a patient wearing the foot and calf support 100 can still bend his or her knee and lift his or her heel.

Additionally, because the adjustment strap 110 is removably or temporarily coupled to the top pad 102 via the securing end 110b, the position of the top pad 102 and thus the size of the space 118 may be adjusted to fit the patient's foot 200. In various embodiments, to insert a patient's foot 200 into the space 118 and adjust the fit of the top pad 102 to fit the patient's foot 200, the securing end 110b of the adjustment strap 110 is first removed from the fastening strip 108. For example, the securing end 110b is pulled away from the fastening strip 108 until a first portion of a hook and loop fastener material on the securing end 110b separates from the complimentary portion of hook and loop fastener material on the fastening strip 108. The adjustment strap 110 is then slid through the adjustment hook 116 to increase the size of the space 118, as illustrated in FIG. 3. Once the patient's foot 200, ankle 202, and calf 204 are positioned as desired onto the calf pad 104 and the foot pad 106, the adjustment strap 110 is pulled through the adjustment hook 116 until the top pad 102 fits snugly on the patient's foot 200 and ankle 202 regions. The securing end 110b of the adjustment strap 110 is then attached to the fastening strip 108 to secure the top pad 102 in the desired position. For example, the securing end 110b is placed onto the fastening strip 108 to refasten the first portion of a hook and loop fastener material on the securing end 110b to the complimentary portion of a hook and loop fastener material of the fastening strip 108. The adjustability of the top pad 102 allows the support 100 to be easily fitted on a patient and allows the patient, for example, to keep slipper socks or a sequential compression device ("SCD") on while wearing the support 100.

As shown in FIGS. 1 and 3, the securing end 110b of the adjustment strap 110 includes a fold 120 (e.g. a fold sewn into the adjustment strap 110). The fold 120 is configured to "catch" on the adjustment hook 116 and thereby prevent the adjustment strap 110 from being inadvertently pulled through the adjustment hook 116. As such, the fold 120 ensures that the top pad 102 cannot be uncoupled from the calf pad 104 and the foot pad 106. Accordingly, the adjustment strap 110 may be pulled and adjusted without the possibility of the adjustment strap 110 sliding completely through the adjustment hook 116 and having to be rethreaded through the adjustment hook 116. Thus, the support 100 may be pulled on the patient's foot 200 and calf 204 like a sock and easily readjusted to fit to the patient's foot 200 and ankle 202 area. Further, in various embodiments, the top pad 102 includes a securing flap 122, as shown in FIG. 3. The securing flap 122 further helps conform the top pad 102 to the patient's foot 200 and ankle 20 in the support 100 and secure the patient's foot 200 and ankle 202 within the space 118.

As shown in FIGS. 2 and 3, the foot pad 106 also includes one or more anti-roll stitches 124. The anti-roll stitches 124 in the foot pad 106 flatten the foot pad 106 such that, when a patient's foot 200 is inserted into the space 118, the patient can stand on the foot pad 106 and even contact the floor or a foot stand through the foot pad 106. Additionally, the anti-roll stitches 124 prevent the foot pad 106 from rolling to one side when pressure is placed on the foot pad 106. For example, if a surgery requires that an operating table be tilted downwards such that patient must stand on a foot support (e.g., a surgery being conducted in a reverse Trendelenburg position), the patient can do so even with the foot and calf support 100 fitted around the patient's foot 200 because the anti-roll stitches 124 allow the patient to stand even while wearing the support 100.

As shown in FIGS. 1-3, an attachment mechanism 126 is also looped through the adjustment hook 116 or otherwise coupled to the support 100. In the embodiment shown, the attachment mechanism 126 is a strap. The attachment mechanism 126 is configured to removably couple or secure the foot and calf support 100 to a fixed object, such as a rail of an operating room table, to maintain the positioning of the support 100 on the support surface. The ability to secure the foot and calf support 100 to a fixed object may be beneficial, as an example, when the support 100 is being used during a surgery and the operating table on which the patient and the support 100 are resting is tilted. The attachment mechanism 126 may accordingly secure the support 100 to the operating room table such that the patient's leg and foot 200 will not slide when the table is moved or tilted.

Figure 4:
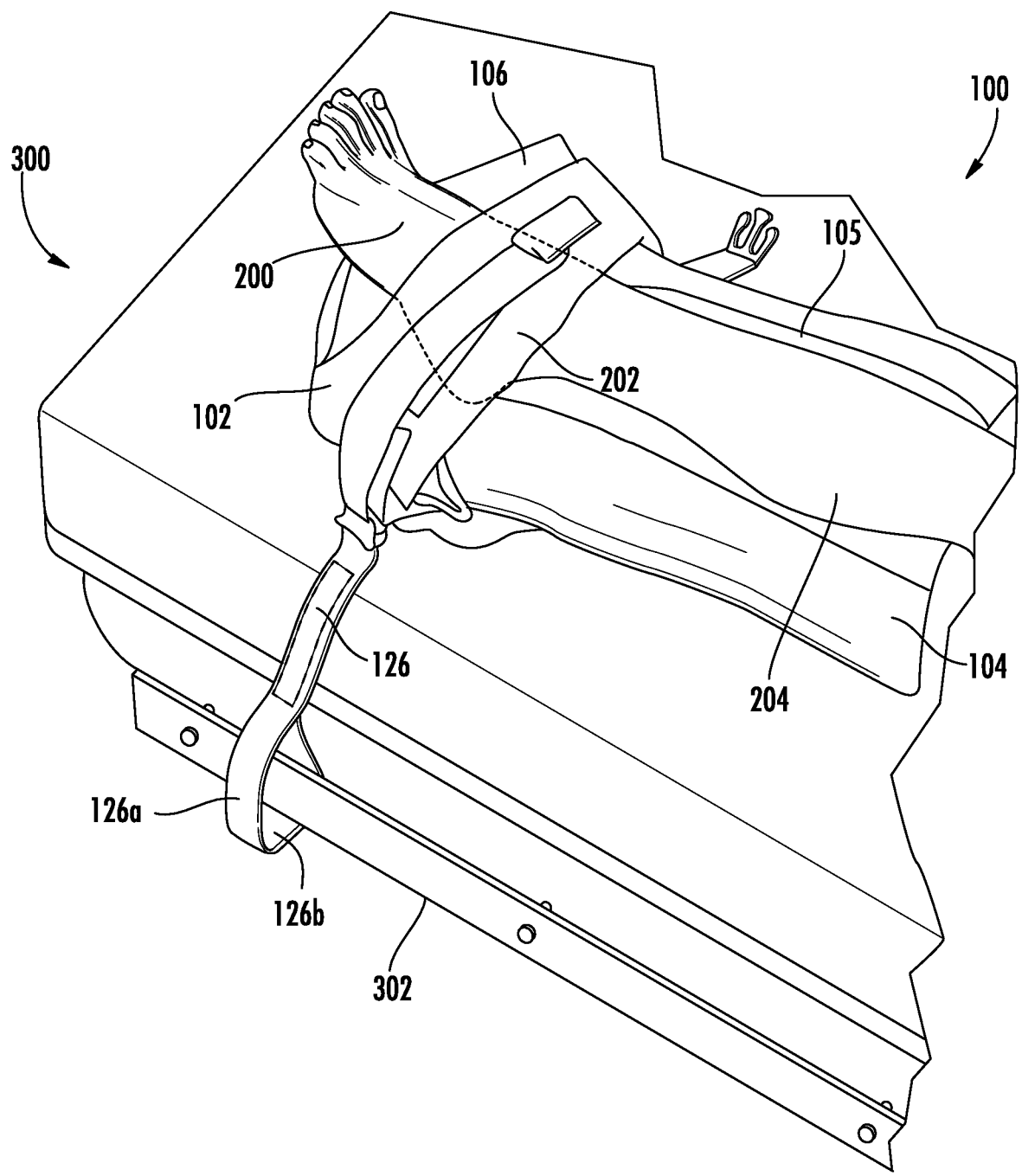
FIG. 4 is a top perspective view of the cushioned foot and calf support of FIG. 1 attached to a table, according to an example embodiment.

Referring to FIG. 4, a top perspective view of the foot and calf support 100 secured to a rail 302 of an operating room table 300 is shown. As shown in FIG. 4, the attachment mechanism 126, shown as a strap, includes an outside surface 126a and an inside surface 126b. The inside surface 126b includes coordinating portions of a fabric hook-and-loop fastener material, such that the inside surface 126b fastens on itself and the strap forms a loop. Thus, to secure the attachment mechanism 126 to the fixed object, such as the rail 302, the hook-and-loop fastener of the inside surface 126b is detached to unloop the strap. The strap is then looped around the fixed object, and the hook-and-loop fastener of the inside surface 126b is reattached to re-secure the strap into a loop. In some embodiments, other securing mechanisms can be used to allow the attachment mechanism 126 to secure the support 100 to a fixed object, including adhesives, snap buttons, zippers, toggles, and the like. Additionally, in some embodiments the attachment mechanism 126 may not be secured to the adjustment hook 116. For example, one end of the attachment mechanism 126 may be secured to the bottom surface 104b of the calf pad 104, and the free end of the attachment mechanism 126 may loop around the fixed object and attach to the secured end of the attachment mechanism 126 to affix the support 100 to the fixed object.

Additionally, as shown in FIGS. 1-3, the second side 104f of the calf pad 104 includes a connecting member 128, shown as a strap, with a first portion of an attachment mechanism, such as a buckle clip 130. In various embodiments, the first portion of the buckle clip 130 coordinates with a second portion of a buckle clip on a second foot and calf support. The first portion of the buckle clip 130 shown in FIGS. 1-3 is a male half, configured to be inserted into a female second portion, though the first portion of the buckle clip 130 may alternatively be a female half and the second portion a male portion. Thus, via the coordinating portions of the buckle clip 130, the support 100 can be buckled to a second support, and two foot and calf supports can be temporarily coupled together. Coupling two supports together may be beneficial because, when coupled, the legs of a patient with a foot 200 secured within each of the coupled supports cannot be inadvertently spread apart. Coupled supports may also prevent the legs of a patient from falling off of the sides of a bed or operating room table. In some embodiments, the foot and calf support 100 may be packaged with or otherwise provided with a second foot and calf support that is similar, the same, or a mirror image of the support 100 (e.g., as shown in FIG. 5).

In other embodiments, another mechanism for coupling two foot and calf supports 100 together may be substituted for the buckle clip 130. For example, two supports 100 may be secured together through ties, hook-and-loop fasteners, snap buttons, zippers, carabiners, and the like. Furthermore, two supports 100 may be provided in a connected arrangement, sharing a connecting member between the two. In such embodiments, the connecting member may be made of a material that is able to be torn, cut, or otherwise released to separate the two supports 100. For example, the connecting member may be a piece of flashspun high-density polyethylene fibers (such as Tyvek) that can be cut or torn by the healthcare professional after use and when the supports 100 are to be uncoupled. In some such embodiments, the connecting member may have a perforated portion to assist with the release of the connecting member.

Additionally, the coupling mechanism may be provided on a different portion of the foot and calf support 100. FIG. 5 illustrates a bottom perspective view of two foot and calf supports 100 coupled together and securing both of a patient's feet 200, according to an exemplary embodiment. FIG. 5 shows a second embodiment of the connecting member 128 and the first portion of the buckle clip 130, where the strap forming the connecting member 128 is configured to wrap around the bottom surface 104b of the calf pad 104. The coordinating portions of the buckle clip 130 for the two supports 100 thus buckle underneath the supports 100 to couple the supports 100 together. Further, one combination of a connecting member 128 and first portion of the buckle clip 130 is configured such that the connecting member 128 is adjustable (e.g., shown as the right strap and female portion of the buckle clip 130 in FIG. 5). In other words, the connecting member 128 may be pulled to shorten the distance between the supports 100 or let out to increase the distance between the supports 100. In various embodiments, once connected together, the connecting members 128 may be releasable (e.g., by unlocking the buckle clip portions 130). The fact that the connecting members 128 may be releasable may be beneficial for practitioners, as the patient may need to be checked on less often when the connecting member 128 are in a released state (e.g., because the connecting members 128 connected together are considered a "restraint" on the patient, which may require that the patient be checked on every fifteen minutes).

Further, in various embodiments, two foot and calf supports 100 may be provided as a kit. For example, the kit may include a first support 100 and a second support 100 that may generally be a mirror image of the first support 100 (e.g., with the exception that the two supports may have slightly different connecting member 128 and buckle clip 130 combinations), as shown in FIG. 5. Providing two mirror image supports 100 as a kit may be beneficial for practitioners, as it may allow them to easily provide supports 100 for both legs of a patient undergoing surgery, where each support is configured to attach to the other (e.g., as shown in FIG. 5) and/or to the operating table (e.g., by the attachment mechanism 126).

In various embodiments, the top pad 102, calf pad 104, and foot pad 106 are filled with a material that provides substantially sturdy support but allows deformation of the top pad 102, calf pad 104, and foot pad 106 when a force is applied. The filling material allows the top pad 102, calf pad 104, and foot pad 106 to retain their original shapes when the force is released. For example, in one embodiment, the top pad 102, calf pad 104, and foot pad 106 are filled with staple fibers (e.g., polyester staple fibers). In another embodiment, the top pad 102, calf pad 104, and foot pad 106 are filled with cluster fibers (e.g., staple fibers that have been formed into spring-like shapes). In still another embodiment the top pad 102, calf pad 104, and foot pad 106 may be filled with, or be constructed out of foam. In yet another embodiment, the top pad 102, calf pad 104, and foot pad 106 may be filled with a non-fiber or foam material, such as air or a gel.

In various embodiments, the surfaces of the top pad 102, calf pad 104, and foot pad 106 are constructed of various materials designed to provide high or low friction when interacting with adjacent surfaces. In one embodiment, the top surface 106a of the foot pad 106 is made of a grip material intended to result in a high friction interaction (i.e., a "high-friction material"), such that a patient's foot 200 is not easily shifted once placed on the foot pad 106. The bottom surface 106b of the foot pad 106 and the bottom surface 104b of the calf pad 104 are made of a second high friction, grip material. The second grip material, however, may result somewhat lower friction than the first grip material used on the top surface 106a of the foot pad 106 such that the second grip material prevents the calf pad 104 and foot pad 106 from being easily shifted once set in place but still allows for adjustments to the positioning of the calf and foot support 100 as needed. For example, the first and second grip materials may be formed of a polyester and/or a nylon (polyamide), such as a rip-stop nylon material (e.g. a nylon material that is woven so that a tear will not spread) or a coated nylon taffeta material that is liquid repellant and/or impermeable and has little to no air permeability while being permeable to moisture vapor.

By contrast, a center portion (e.g., an approximately 10 cm center strip, shown in FIG. 1 as the center portion 105 of the top surface 104a of the calf pad 104) of the top surface 104a of the calf pad 104 may be made of a material that results in a low friction interaction with adjacent surfaces (i.e., a "low-friction material"), slightly deformable material such as spandex. The low-friction material allows the patient's foot 200, ankle 202, and calf 204 to be easily slid into place on the foot and calf support 100. Additionally, the low-friction, slightly deformable material conforms to the patient's calf 204 and ankle 202 to keep the patient's leg centered and cradled on the calf pad 104 and in the foot and calf support 100. In this way, the center portion 105 creates a cradle and hammock for better distribution of pressure on the patient's calf 204 and ankle 202. The rest of the top surface 104a of the calf pad 104 may be made of a rip-stop material. Further, the top pad 102, may be made of a low-friction, breathable material to allow the top pad 102 to be easily positioned on top of the patient's foot 200 and prevent the patient's foot 200 and calf 204 from becoming uncomfortable due to breathability issues.

In other embodiments, the top pad 102, calf pad 104, and foot pad 106 may be made of more, fewer, or different materials. For example, in certain embodiments, the top pad 102, calf pad 104, and foot pad 106 (aside from the center portion 105) may be made of a non-woven material to highlight to disposability of the support 100 (e.g., to encourage a single use, rather than multiple uses, of the support 100). As another example, the top pad 102, calf pad 104, and foot pad 106 may all be made of the same nylon material. As yet another example, the top pad 102, calf pad 104, and foot pad 106 may all be made of the same material, but portions of the surfaces of top pad 102, calf pad 104, and/or foot pad 106 may be treated to include one or more textures, coatings, additives, and/or other elements that increase or decrease the friction properties of the treated surfaces. Further, as will be appreciated, some or all of the materials used in the foot and calf support 100 may have rip-stop properties and may have suitable structural strength and stability to form the support 100. The materials may also be treated with a water repellant, such as polytetrafluoroethylene (PTFE), and may be low-linting fabrics.

Figure 6:
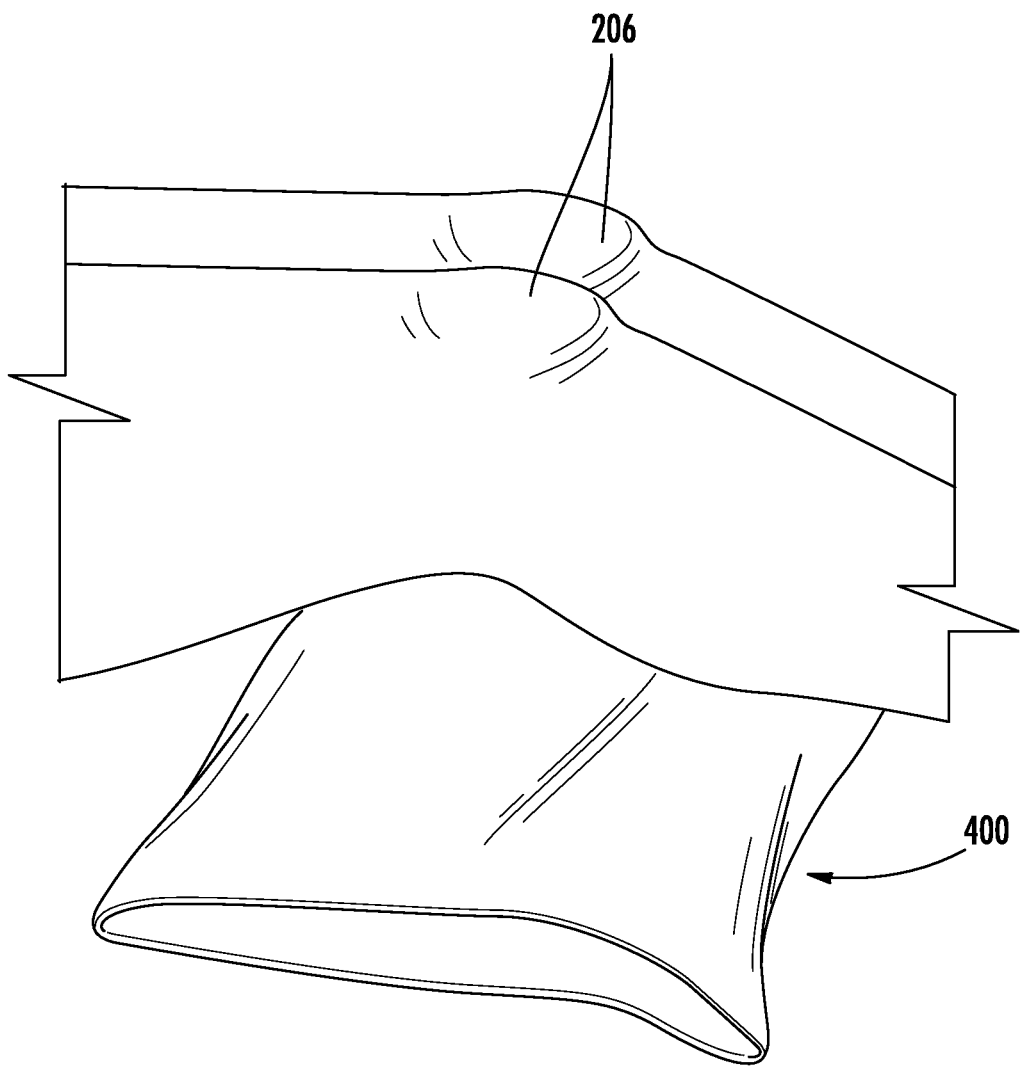
FIG. 6 is a perspective view of a knee support pillow, according to an exemplary embodiment.

In various embodiments, the foot and calf support 100 is used in conjunction with a knee support pillow 400. FIG. 6 is a perspective view of the knee support pillow in use, according to an exemplary embodiment. The knee support pillow 400 is sized and shaped to fit under both knees 206 of a patient such that the knees 206 maintain a slight bend. Conversely, in some embodiments, the knee support pillow 400 is sized and shaped to fit under a single knee 206 of the patient. Accordingly, the knee support pillow 400 or knee support pillows 400 are configured to prevent hyperextension of the patient's knees 206 and keep the knees 206 bent (e.g., a minimum of 5-10°) to ensure circulation. One or more knee support pillows 400 may also be provided in a kit with one or more foot and calf supports 100.

Figure 7:
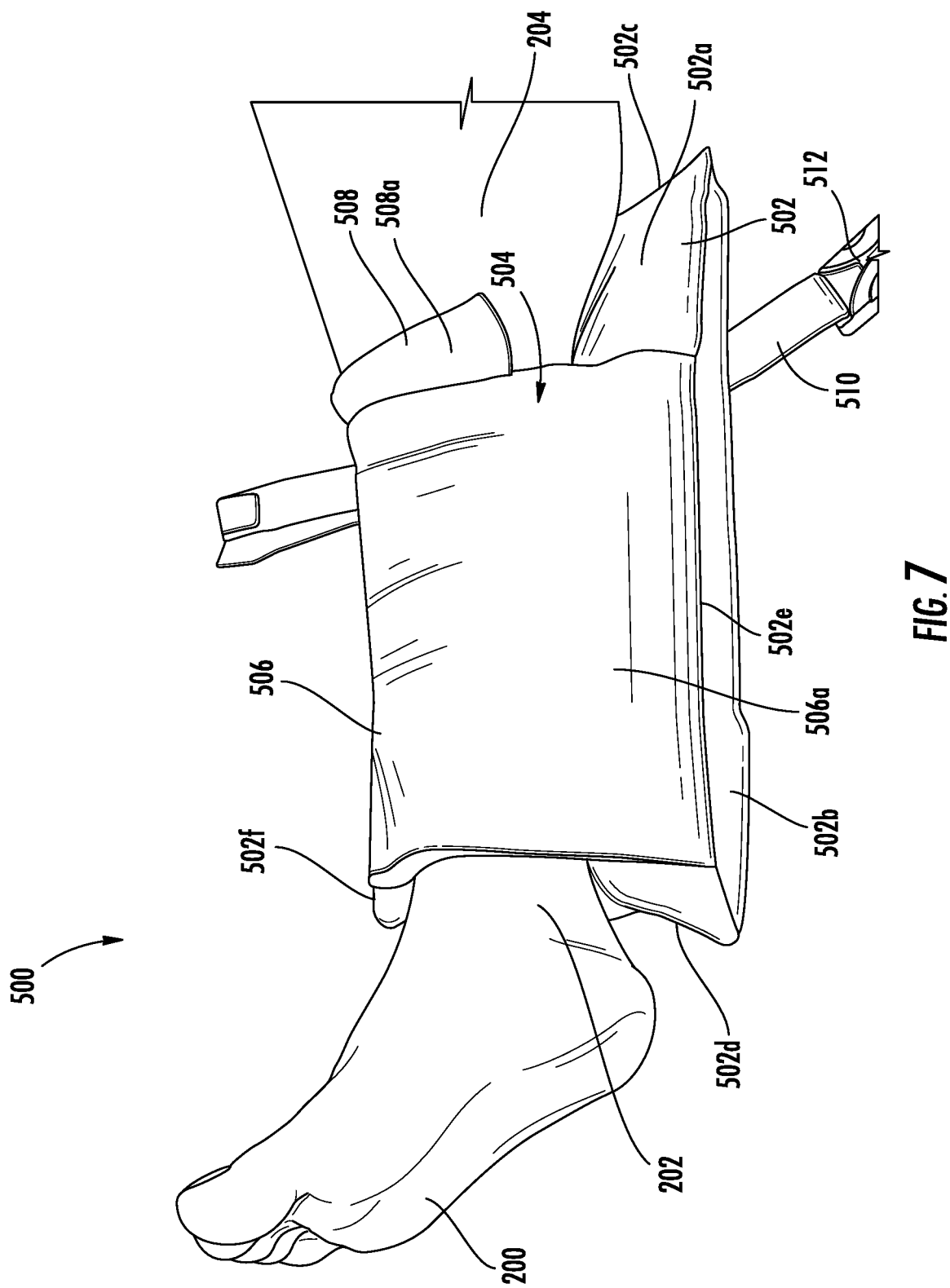
FIG. 7 is a side perspective view of a cushioned calf support, according to an exemplary embodiment.

Referring to FIG. 7, a perspective view of a cushioned calf support 500 is shown, according to another exemplary embodiment. As shown in FIG. 7, the calf support 500 is formed of a single calf pad 502. However, it will be appreciated that while the calf pad 502 is described herein as a single component, multiple pads may be used to form the pad 502. As shown in FIG. 7, outer edges of the calf pad 502 form a rectangular or oblong shape, though in other embodiments, the outer edges of the calf pad 502 may form a different shape such an elliptical shape, or the calf pad 502 may be cylindrical. The calf pad 502 includes a top surface 502a and a bottom surface 502b (shown in FIG. 10) opposite from the top surface 502a. The calf pad 502 also includes proximal end 502c, a distal end 502d, a first side 502e, and a second side 502f formed where the top surface 502a meets the bottom surface 502b, with the proximal end 502c opposite the distal end 502d and the first side 502e opposite the second side 502f. In various embodiments, the calf pad 502 is created similarly to the top pad 102, as described above.

Figure 8:
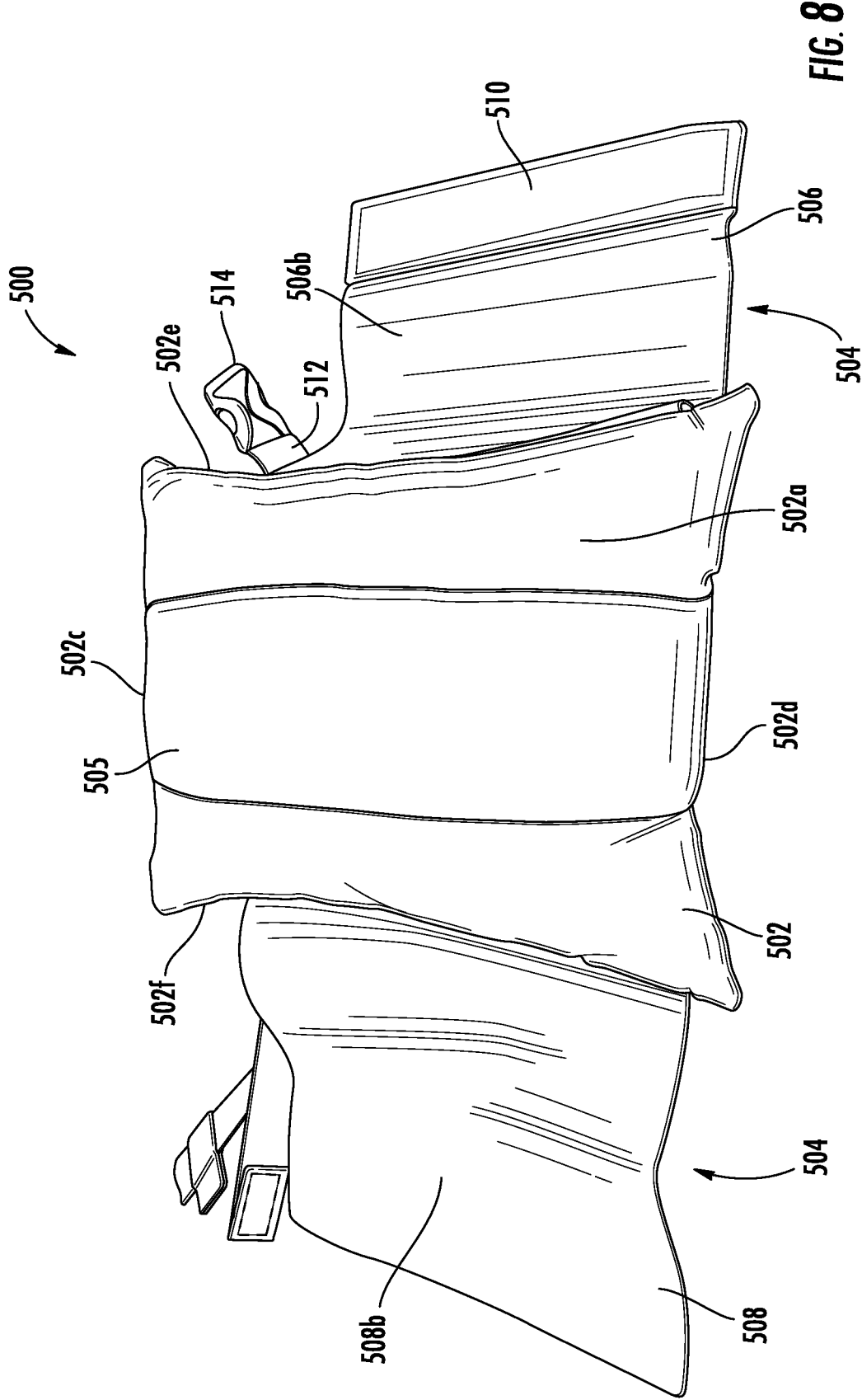
FIG. 8 is a top perspective view of the cushioned calf support of FIG. 7, according to an exemplary embodiment.

As further shown in FIG. 7, the support 500 includes a leg wrap 504 having a first flap 506 and a second flap 508. The first flap 506 includes an outer surface 506a, and the second flap 508 includes an outer surface 508a. The first flap 506 also includes an inside surface 506b, and the second flap 508 includes an inside surface 508b, as illustrated in FIG. 8, which shows a top perspective view of the leg wrap 504 in an unfastened state. As shown in FIG. 7, the outer surface 508a of the second flap 508 includes, or is made of, a fastening material such as a fabric loop material. Similarly, as shown in FIG. 8, the inside surface 506b of the first flap 506 includes a fastening strip 510 configured to removably fasten to the fastening material of the outer surface 508a of the second flap 508. For example, the fastening strip 510 may be made of a fabric hook material that removably attaches to the fabric loop material on the outer surface 508a, or vice versa.

In this way, the leg wrap 504 may be unfastened, as shown in FIG. 8, to allow a patient's calf 204 to be placed on the calf pad 502. Referring back to FIG. 7, when the patient's calf 204 is placed in the cushioned calf support 500, the patient's calf 204 rests on the top surface 502a of the calf pad. For example, the patient's calf 204 may rest on a center portion 505 of the calf pad 502 made of a slightly deformable material (e.g., spandex) configured to conform to the patient's calf 204. The second flap 508 and the first flap 506 of the leg wrap 504 may then be wrapped over the patient's leg and fastened together to secure the patient's calf 204 into the support 500. Additionally, because the first flap 506 is configured to removably attach to the second flap 508, the leg wrap 504 may be adjusted to accommodate varying sizes of patient calves 204 by adjusting the placement of the fastening strip 510 on the outer surface 508a of the second flap 508. Furthermore, because the leg wrap 504 is adjustable, the leg wrap 504 may be used for a patient wearing a sequential compression device (SCD) or other compression device.

In other embodiments, the calf support 500 may instead include a different securing system configured to secure a portion of a patient's leg to the calf pad 502. For example, the support 500 may include a top pad and/or a foot pad, similar to the top pad 102 and the foot pad 106 described above with reference to FIGS. 1-3, configured to secure the portion of the patient's leg to the calf pad 502. As another example, the support 500 may instead include an expandable sleeve attached to the calf pad 502 that stretches to accommodate the portion of the patient's leg and secure the portion of the patient's leg to the calf pad 502.

Figure 9:
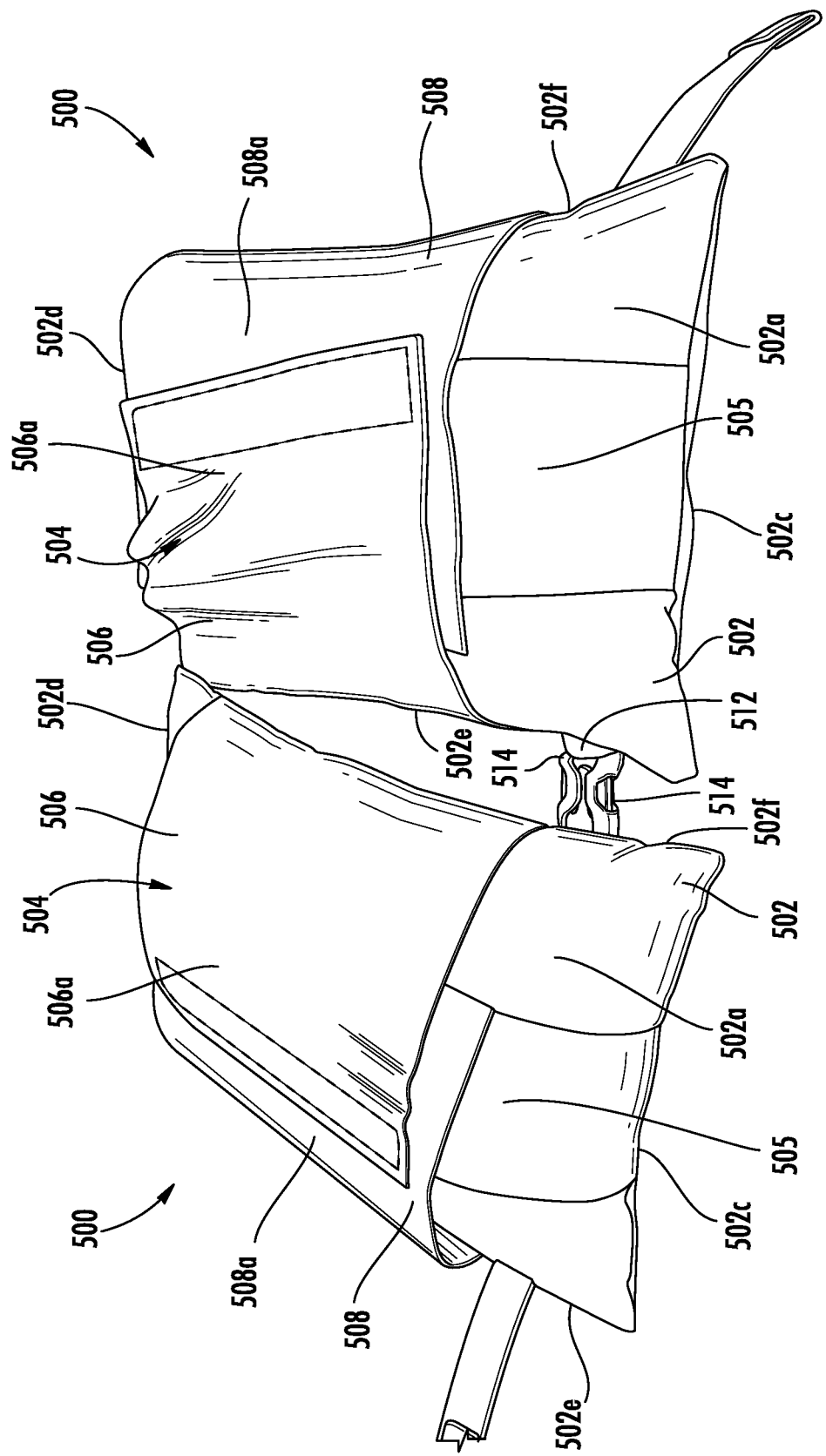
FIG. 9 is a top perspective view of two connected calf supports, according to an exemplary embodiment.
Figure 10:
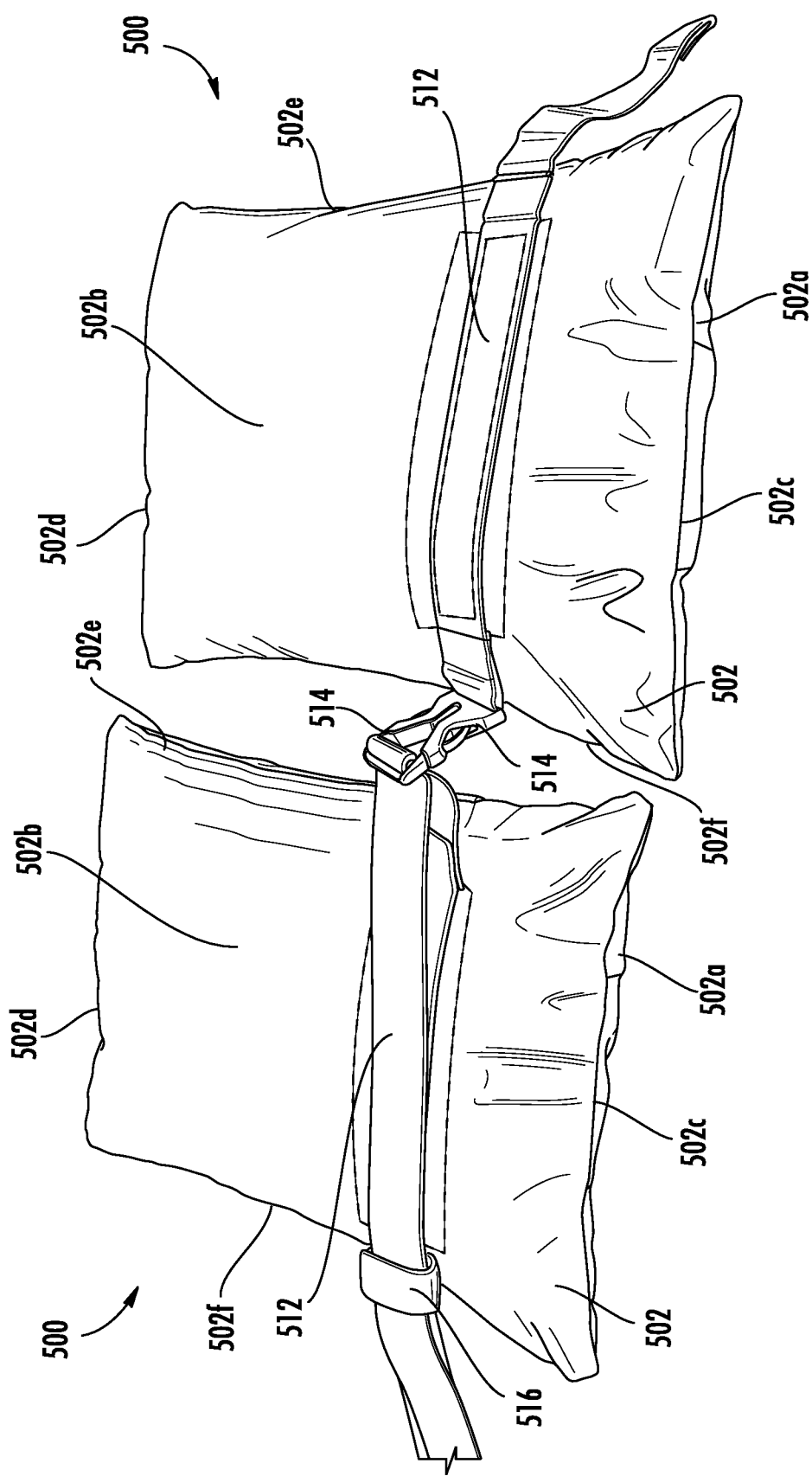
FIG. 10 is a bottom perspective view of the two connected calf supports of FIG. 9, according to an exemplary embodiment.

In various embodiments, the calf pad 502 includes an attachment mechanism similar to the attachment mechanism 126 discussed above with respect to FIGS. 1-4. Additionally, in various embodiments, the calf pad 502 includes a connecting member 512 with a first portion of a buckle clip 514, as shown in FIGS. 7 and 8. As such, similar to the connecting member 128 and first portion of the buckle clip 130 discussed above with reference to FIGS. 1-5, the connecting member 512, shown as a strap, may be attached to a second connecting member via the first portion of the buckle clip 514 engaging with a second portion of a buckle clip. In this way, the support 500 can be buckled to a second support, and two calf supports can thereby be temporarily coupled together. FIG. 9 illustrates a top perspective view of two supports 500 buckled together in this manner. FIG. 10 illustrates a bottom perspective view of the two supports 500 buckled together. As shown in FIG. 10, in some embodiments, the connecting member 512 may be configured similarly to the connecting member 128 such that the connecting member 512 is configured to wrap around the bottom surface 502b of the calf pad 502. In such embodiments, the portions of the buckle clip 514 for the two supports 500 buckle underneath or between the supports 500 to couple the supports 500 together.

Further, in various embodiments, at least one of the combination of the connecting member 512 and first portion of the buckle clip 514 is configured such that the connecting member 512 is adjustable (e.g., shown as the left connecting member 512 and female portion of the buckle clip 514 in FIG. 10). In other words, the connecting member 512 may be pulled to shorten the distance between the supports 500 or let out to increase the distance between the supports 500. Additionally, the calf support 500 with the adjustable connecting member 512 may include a strap loop 516 for maintaining the excess connecting member 512 in place. In various embodiments, once connected together, the connecting members 512 may be releasable (e.g., by unlocking the buckle clips 514).

In some embodiments, two supports 500 may be secured together using connecting members having other releasable coupling mechanisms, such as through ties, hook-and-loop fasteners, snap buttons, zippers, carabiners, and the like. Furthermore, two supports 500 may be provided in a connected arrangement, sharing a connecting member between the two. In such embodiments, the connecting member may be made of a material that is able to be torn, cut, or otherwise released to separate the two supports 500. For example, the connecting member may be a piece of flashspun high-density polyethylene fibers (such as Tyvek) that can be cut or torn by the healthcare professional after use and when the supports 500 are to be uncoupled. In some such embodiments, the connecting member may have a perforated portion to assist with the release of the connecting member.

In various embodiments, similar to the foot and calf support 100, two supports 500 may be provided as a kit, for example, with a first support 500 and a second support 500 that is generally a mirror image of the first support 500. As an example, the calf supports 500 shown in FIGS. 9 and 10 may be provided in a kit. Additionally, the calf supports 500 may be used in conjunction with one or more knee support pillows, as discussed above with respect to FIG. 6, and may further be provided in a kit with one or more knee support pillows.

In various embodiments, the pad 502 may be filled similarly to the top pad 102, calf pad 104, and foot pad 106 discussed above. In other embodiments, the pad 502 may be formed by some other method using another material such as molded or formed foam. The pad 502 may also be constructed of similar materials as discussed with respect to the top pad 102, calf pad 104, and foot pad 106. For example, the top surface 502a of the calf pad 502 may include a center portion (e.g., shown in FIGS. 8 and 9 as the center portion 505 of the top surface 502a of the calf pad 502) made of a low-friction, slightly deformable material such as spandex. The rest of the top surface 502a of the calf pad 502 may be made of a rip-stop material (e.g. a nylon material that is woven so that a tear will not spread), while the bottom surface 502b of the calf pad 502 may be made of a high-friction grip material to prevent the calf pad 502 from sliding. As another example, the rest of the top surface 502a and/or the bottom surface 502b of the calf pad 502 may be made of a non-woven material to highlight the disposability of the calf pad 502 (e.g., to encourage a single use, rather than multiple uses, of the support 500).

Figure 11:
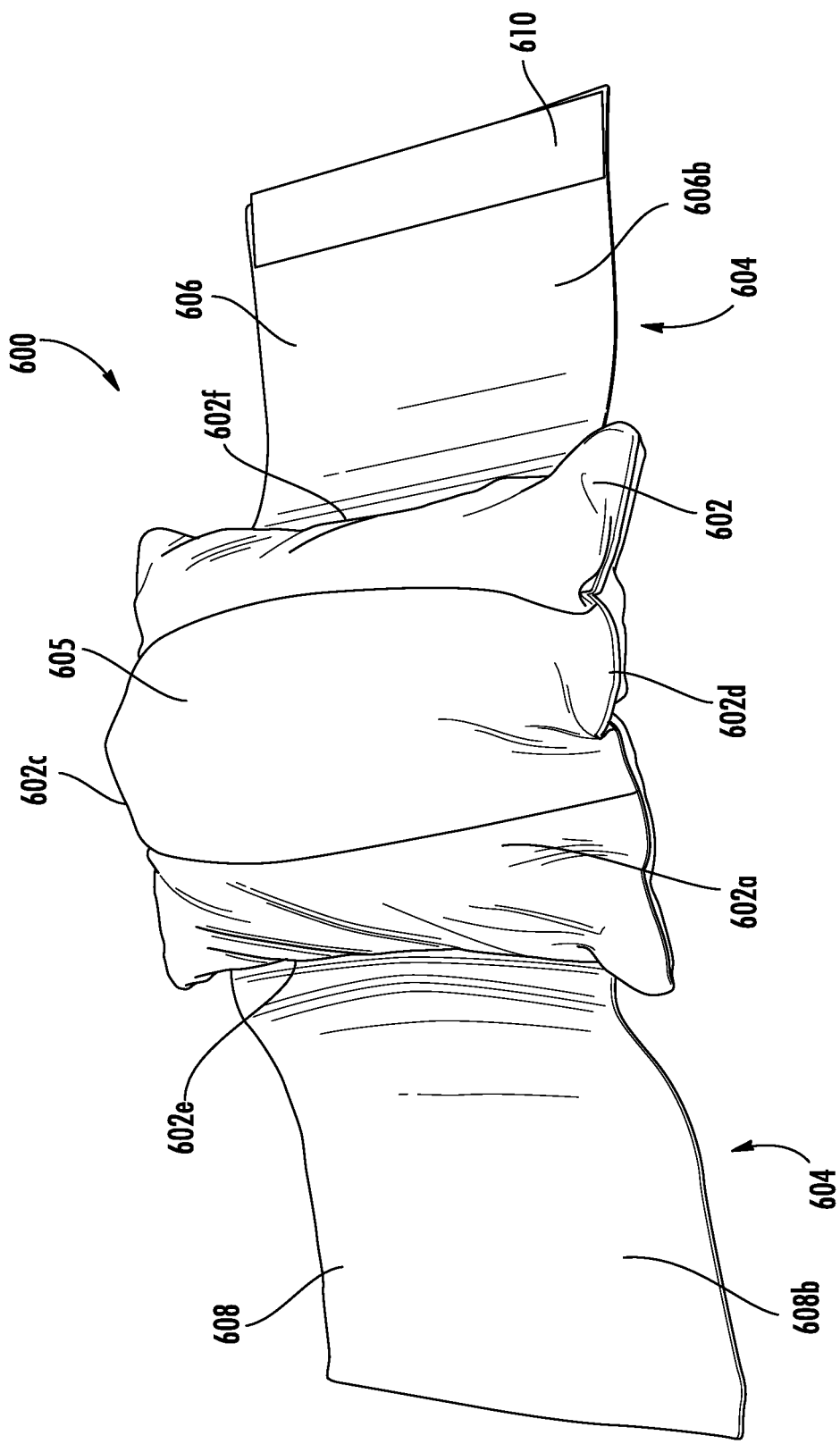
FIG. 11 is a top perspective view of a cushioned calf support, according to an exemplary embodiment.

Referring to FIG. 11, a top perspective view of a cushioned calf support 600 is shown, according to another exemplary embodiment. As shown in FIG. 11, outer edges of the calf pad 602 form a rectangular or oblong shape, though in other embodiments, the outer edges of the calf pad 602 may form a different shape such as an elliptical shape or the calf pad 602 may be cylindrical. The calf pad 602 includes a top surface 602a and a bottom surface 602b (shown in FIG. 12) opposite from the top surface 602a. The calf pad 602 also includes a proximal end 602c, a distal end 602d, a first side 602e, and a second side 602f formed where the top surface 602a meets the bottom surface 602b, with the proximal end 602c opposite the distal end 602d and the first side 602e opposite the second side 602f.

Figure 12:
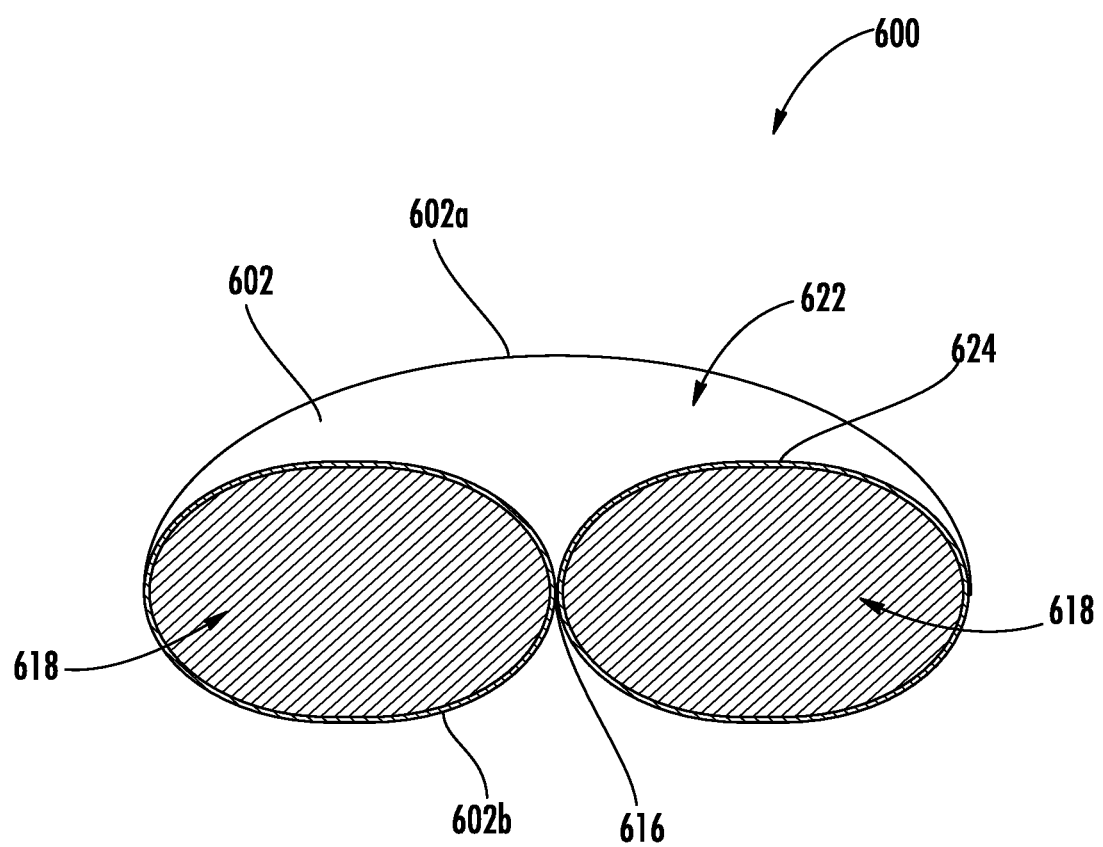
FIG. 12 is a cross-sectional view of the cushioned calf support of FIG. 11, according to an embodiment.

Referring to FIG. 12, a cross-sectional view of the cushioned calf support 600 taken along a lateral central axis of the support 600 is shown, according to an exemplary embodiment. As shown in FIG. 12, the calf support 600 is formed from two pontoons 618 covered by a top pillow 622. In various embodiments, the pontoons 618 serve to elevate a patient's leg and foot while preventing settling of the leg and foot onto the pad 602 during a procedure. For example, the pontoons 618 may elevate the patient's leg and foot such that a separation between the patient's heel and an operating room table is maintained during a procedure (e.g., a separation large enough to run fingers under the patient's heel). However, it should be understood that, while in the embodiment of FIG. 12 the pad 602 includes two pontoons 618, in other embodiments the pad 602 may include more than two pontoons 618.

Figure 14:
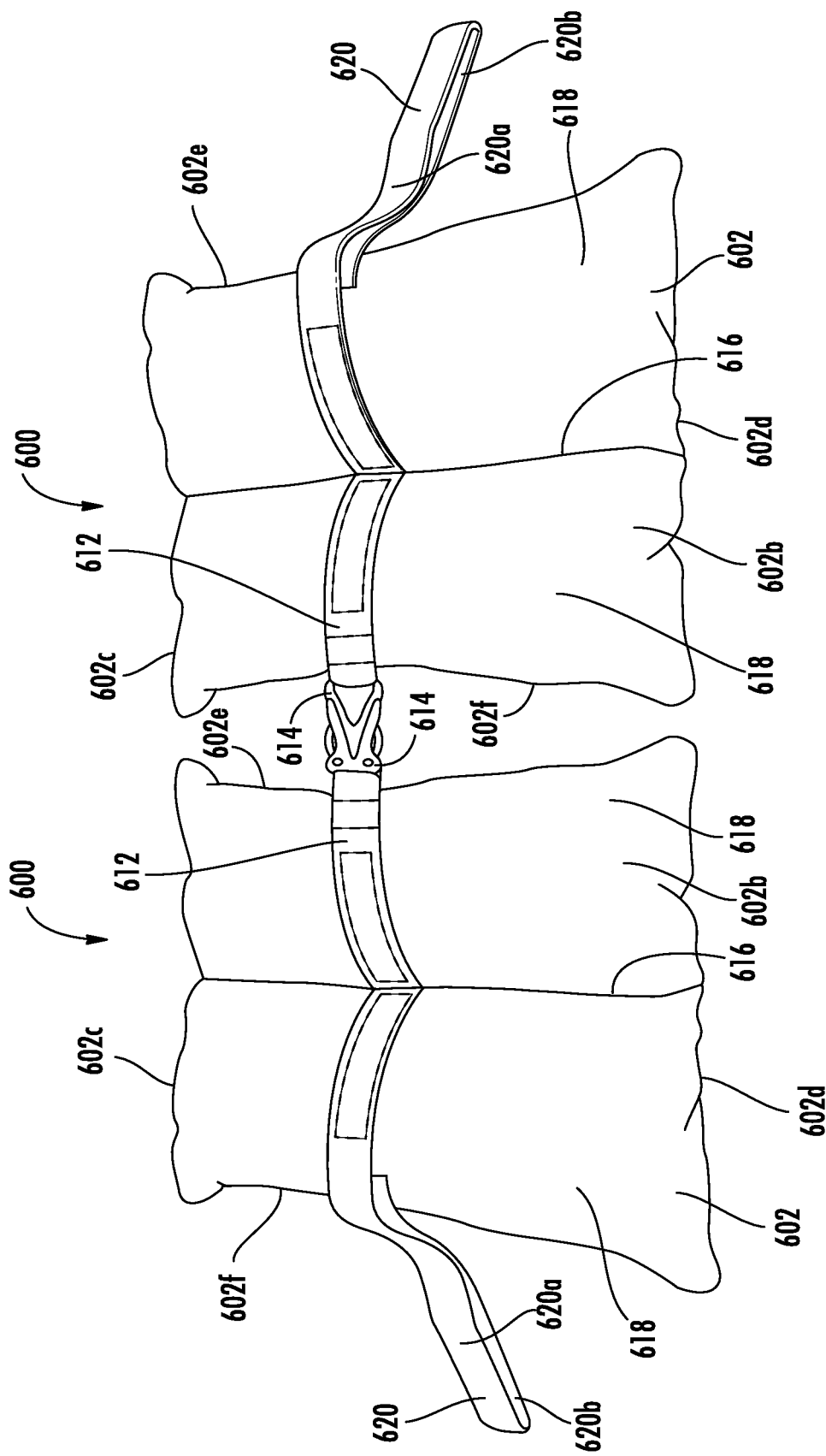
FIG. 14 is a bottom perspective view of the two connected calf supports of FIG. 13, according to an exemplary embodiment.

As illustrated in FIG. 12, in some embodiments, the pad 602 is created by stitching the bottom surface 602b to an intermediate surface 624 at a line 616 down the center of the connected bottom surface 602b and intermediate surface 624 to form the pontoons 618 (e.g., as shown in greater detail in FIG. 14). Filling material is inserted into the pontoons 618 between the bottom surface 602b and the intermediate surface 624. The top surface 602a is stitched over the intermediate surface 624, and filling material is inserted between the top surface 602a and the intermediate surface 624 to form the top pillow 622. When constructed in this way, a bottom portion of the pad 602 includes pontoons 618 that provide a cradling effect for a foot or leg placed on the top surface 602a of the pad 602. The pontoons 618 also elevate the foot or leg. Preferably, the pontoons 618 elevate the heel enough such that a practitioner can see the patient's heel and visually assess the lifting of the heel and foot from a distance. The top pillow 622 distributes pressure across the foot or leg substantially evenly such that the patient does not experience pressure hot spots on the sides of the patient's foot or leg. Additionally, the separately constructed pontoons 618 prevent the filling material from settling when the foot or leg is placed on the top pillow 622. For example, the pad 602, is configured to allow a maximum of about 4,300 N/m2 or about 32 mmHG of pressure on the heel or Achilles tendon.

In other embodiments, the pad 602 may be created in a different manner. For example, the pad 602 may be created similarly to the top pad 102, namely, by stitching the line 616 down the center of the bottom surface 602b and stitching the top surface 102a and the bottom surface 102b together. Filling material (e.g., poly-fill) may then be inserted between the top surface 102a and the bottom surface 102b before the top surface 102a and the bottom surface 102b are completely stitched together. In other embodiments, the pad 602 may be formed by some other method using another material such as molded or formed foam.

Similar to the top pad 102, calf pad 104, and foot pad 106, the pad 602 is filled with a material that provides substantially sturdy support but allows deformation of the pad 602 when a force is applied. The filling material also allows the pad 602 to retain its original shape when the force is released. Accordingly, in various embodiments, similar to the top pad 102, calf pad 104, and foot pad 106, the pad 602 is filled with staple fibers (e.g., polyester staple fibers), cluster fibers (e.g., polyester cluster fibers), foam, air, gel, or another material that provides support but allows for deformation. In some embodiments, the filling material inserted between the top surface 602a and the intermediate surface 624 to form the top pillow 622 may be different from the filling material inserted into the pontoons 618. In an embodiment, the top pillow 622 may be filled at a different density from the pontoons 618. For example, the pontoons may be filled to a first density, and the top pillow 622 may be filled to a second density that is less than the first density. Filling the pad 602 in this manner may allow the pontoons 618 to effectively support the portion of the patient's leg on the pad 602, with the top pillow 622 cradling the portion of the patient's leg and spreading the support pressure across the portion of the patient's leg due to its lesser filling density.

Figure 13:
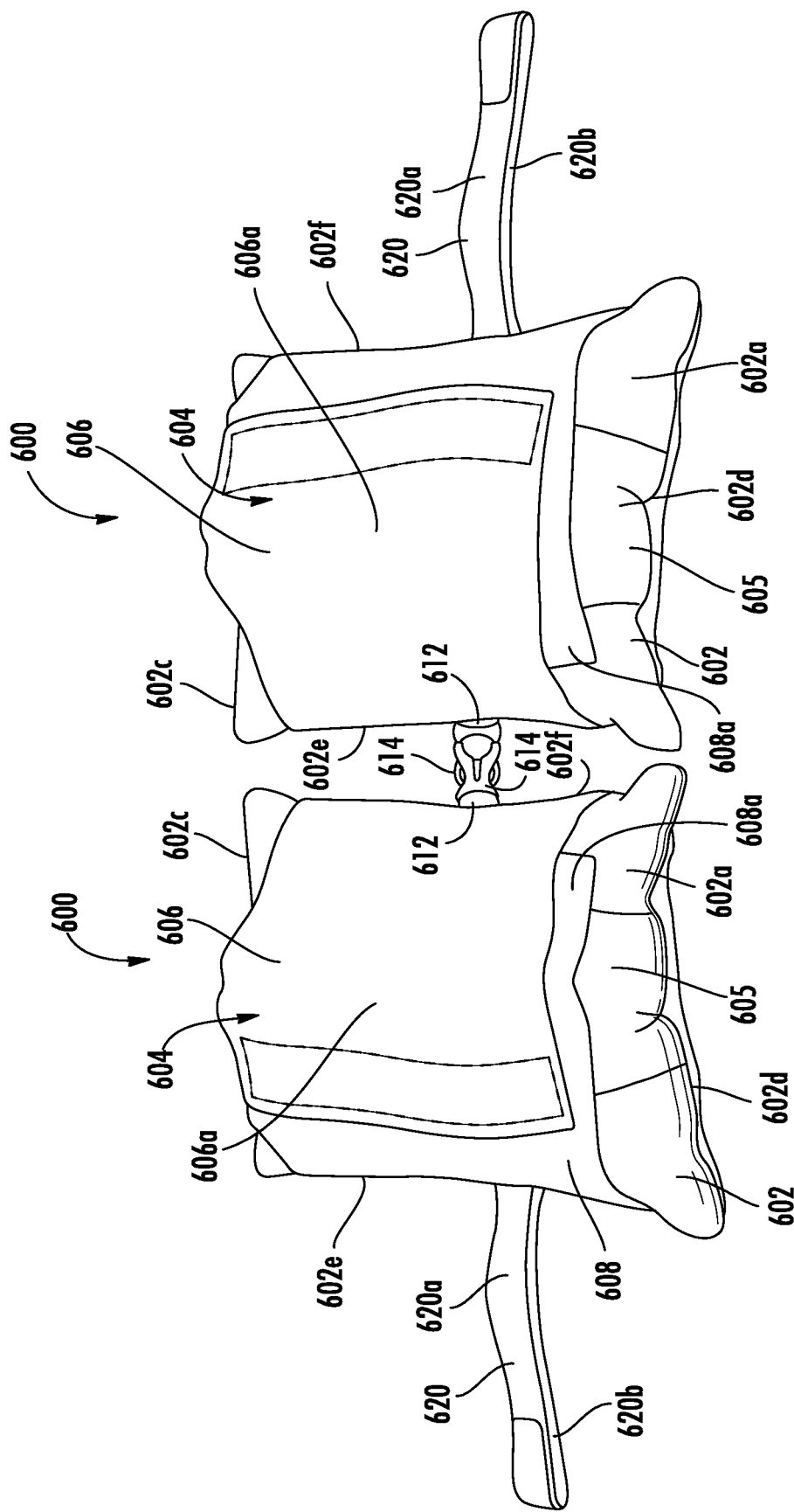
FIG. 13 is a top perspective view of two connected calf supports, according to an exemplary embodiment.

Referring back to FIG. 11, the pad 602 also includes a leg wrap 604 having a first flap 606 and a second flap 608. The first flap 606 includes an outer surface 606a, and the second flap includes an outer surface 608a, as illustrated in FIG. 13, which shows a top perspective view of two pads 602 with leg wraps 604 in fastened states. Additionally, the first flap 606 includes an inside surface 606b, and the second flap 608 includes an inside surface 608b, as illustrated in FIG. 11. In various embodiments, at least the inside surface 608b of the second flap is made of an extendable material configured to conform to a portion of a patient's leg, such as double-layer spandex. Further, as shown in FIG. 13, the outer surface 608a of the second flap 608 includes, or is made of, a fastening material such as a fabric loop material. Similarly, as shown in FIG. 11, the inside surface 606b of the first flap 606 includes a fastening strip 610 configured to removably fasten to the fastening material of the outer surface 608a of the second flap 608. For example, the fastening strip 610 may be made of a fabric hook material that removably attaches to the fabric loop material on the outer surface 608a, or vice versa.

In this way, the leg wrap 604 may function similarly to the leg wrap 504 of the calf pad 502. For example, the leg wrap 604 may be unfastened as shown in FIG. 11 to allow a patient's calf to be placed on the calf pad 602. The patient's calf may rest on a center portion 605 of the calf pad 602 made of a slightly deformable material (e.g., spandex) configured to conform to the patient's calf. The second flap 608 and the first flap 606 of the leg wrap 604 may then be folded and fastened together over the patient's leg to secure the patient's calf into the support 600 and subsequently adjusted as necessary. In other embodiments, however, the calf support 600 may instead include a different securing system configured to secure a portion of the patient's leg to the calf pad 602, such as a top pad and/or foot pad similar to the top pad 102 and the foot pad 106, described above with reference to FIGS. 1-3, or an expandable sleeve.

Referring to FIG. 13, in various embodiments, the calf pad 602 includes an attachment mechanism 620 similar to the attachment mechanism 126 discussed above with respect to FIGS. 1-4. The attachment mechanism 620, shown as a strap, includes an outside surface 620a and an inside surface 620b. The inside surface 620b includes coordinating portions of a fabric hook-and-loop fastener material, such that the inside surface 620b fastens in on itself and the strap forms a loop. Thus, the attachment mechanism 620 can be secured to a fixed object as described above with reference to FIG. 4. In this way, the pad 602 may be connected to an operating room table (e.g., similarly to the support 100 connected to the rail 302 of the operating room table 300 shown in FIG. 4), to maintain the position of the calf pad 602 on the support surface, such that the pad 602 can be subjected to tilting of the operating room table without sliding off. Additionally, because the pad 602 is configured such that the patient's heel is free, the operating room table can be tilted to move the patient into a standing position.

Further, in various embodiments, the calf pad 602 includes a connecting member 612, shown as a strap, with a first portion of a buckle clip 614, as shown in FIG. 13. As such, similar to the connecting member 128 and the first portion of the buckle clip 130 discussed above with reference to FIGS. 1-5, the connecting member 612 may be attached to a second coupling strap via the first portion of the buckle clip 614 engaging with a second portion of a buckle clip. In this way, the support 600 can be buckled to a second support, and two calf supports 600 can thereby be temporarily coupled together. FIG. 13 illustrates a top perspective view of two supports 600 buckled together in this manner. FIG. 14 illustrates a bottom perspective view of two supports 600 buckled together in this manner, and as shown, in some embodiments, the connecting member 612 is configured to wrap around the bottom surface 602b of the calf pad 602. In such embodiments, the portions of the buckle clip 614 for the two supports 600 buckle underneath or between the supports 600 to couple the supports 600 together.

In some embodiments, at least one of the combinations of connecting member 612 and first portion of the buckle clip 614 is configured such that the connecting member 612 is adjustable. However, in other embodiments, neither connecting member 612 is adjustable. For example, the support 600 may be sized to be large enough (e.g., about 30 cm or 11.5 inches wide) such that two supports 600 coupled together side-by-side take up nearly the entire width of an operating room table or hospital bed and thus, no adjustability is needed. In various embodiments, the connecting members 612 may also be releasable (e.g., by unlocking the buckle clips 614). Further, in some embodiments, two supports 600 may be secured together through releasable coupling mechanisms other than the buckle clips 614, such as ties, hook-and-loop fasteners, snap buttons, zippers, carabiners, and the like. Furthermore, two supports 600 may be provided in a connected arrangement, sharing a connecting member between the two. In such embodiments, the connecting member may be made of a material that is able to be torn, cut, or otherwise released to separate the two supports 600. For example, the connecting member may be a piece of flashspun high-density polyethylene fibers (such as Tyvek) that can be cut or torn by the healthcare professional after use and when the supports 600 are to be uncoupled. In some such embodiments, the connecting member may have a perforated portion to assist with the release of the connecting member.

Figure 15:
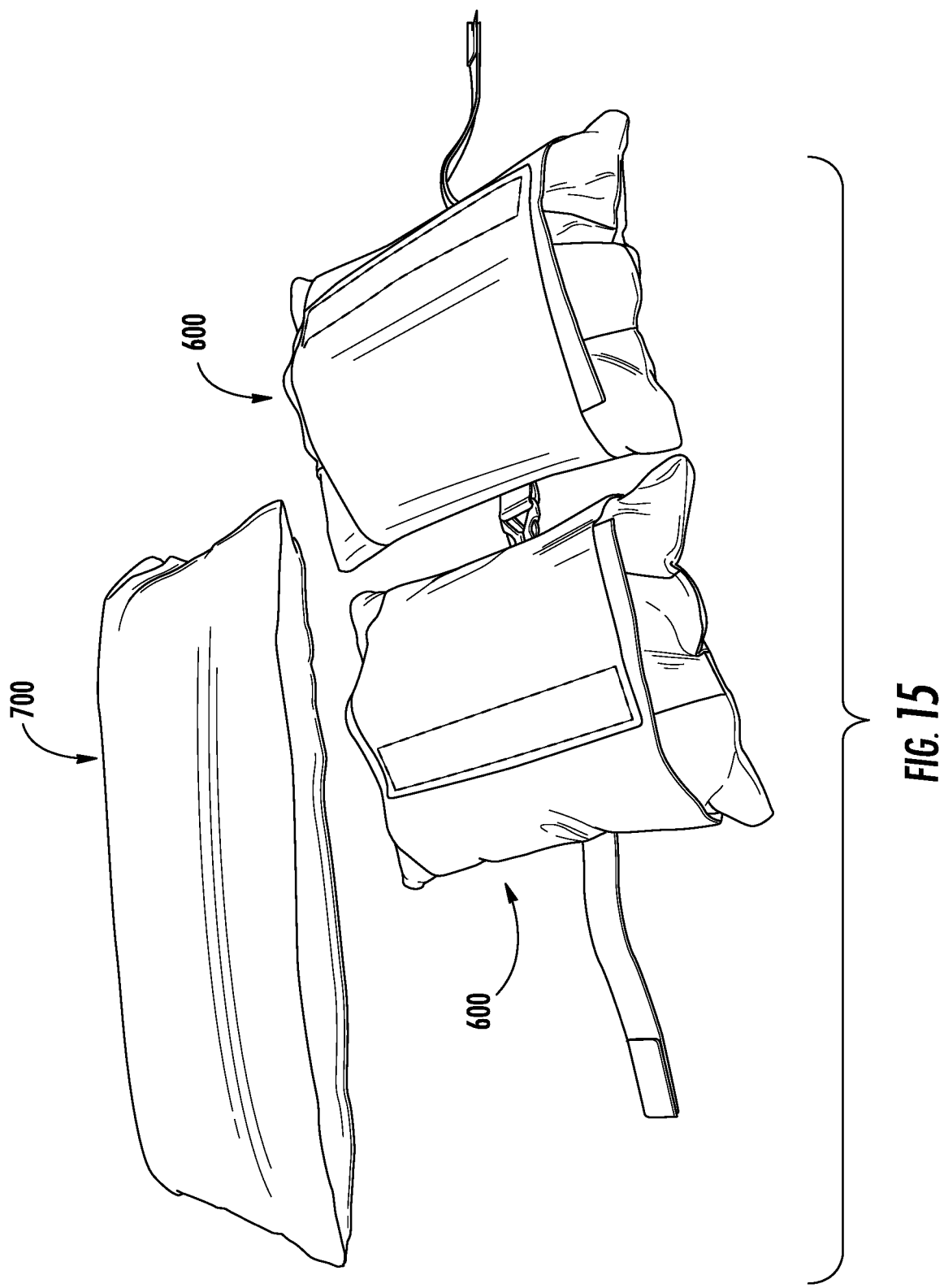
FIG. 15 is a top perspective view of the two calf supports of FIG. 13 and a knee support pillow, according to an exemplary embodiment.

In various embodiments, similar to the foot and calf support 100, two supports 600 may be provided as a kit, for example, with a first support 600 and a second support 600 that differ only in the portion of the buckle clip provided on the connecting member 612. As an example, the calf supports 600 shown in FIGS. 13 and 14 may be provided in a kit. Additionally, the calf supports 600 may be used in conjunction with one or more knee support pillows, as discussed above with respect to FIG. 6, and may further be provided in a kit with one or more knee support pillows. For example, according to one embodiment, the calf supports 600 may be provided in a kit with a knee support pillow 700, as shown in FIG. 15. As shown in FIG. 15, the knee support pillow 700 is as wide or wider that the combined widths of the two calf supports 600. Accordingly, in some arrangements, the two calf supports when arranged side-by-side are as wide as an operating room table or hospital bed, and the knee support pillow 700 is equal to the width or slightly longer than the width of the table or bed. Additionally, the calf supports 600 and the knee support pillow 700 may be configured such that the lengths and heights of the calf supports 600 and the knee support pillow 700 can be used with patients of a variety of heights. As an illustration, for a shorter patient, the calf supports 600 and the knee support pillow 700 may be configured such that the knee support pillow 700 may be pushed against the proximal ends 602c of the supports 600 and still support the knees of the patient and elevate the patient's heels above the table or bed. However, for a taller patient, the calf supports 600 and knee support pillow 700 may be separated to support the knees of the patient and elevate the patient's heels above the table or bed.

In various embodiments, the pad 602 may be constructed of similar materials as discussed with respect to the top pad 102, calf pad 104, and foot pad 106. For example, the top surface 602a of the calf pad 602 may include a center portion (e.g., shown in FIGS. 11 and 13 as the center portion 605 of the top surface 602a of the calf pad 602) made of a low-friction, slightly deformable material such as spandex. The rest of the top surface 602a of the calf pad 602 may be made of a rip-stop material (e.g. a nylon material that is woven so that a tear will not spread), while the bottom surface 602b of the calf pad 602 may be made of a high-friction grip material to prevent the calf pad 602 from sliding. As another example, the rest of the top surface 602a and/or the bottom surface 602b of the calf pad 602 may be made of a non-woven material to highlight the disposability of the calf pad 602 (e.g., to encourage a single use, rather than multiple uses, of the support 600).

Any of the elements described above with respect to cushioned support devices 100, 500, and 600, and kits made thereof, may be sterilized during or after production, and prior to being distributed to health care facilities. Sterilization of the devices may be performed using any sterilization means, such as the use of gamma radiation, electron-beam radiation, X-ray radiation, Ethylene oxide (EtO), steam, such as through the use of an autoclave, or any combination thereof.

Though the foregoing cushioned support devices 100, 500, and 600 are intended for single use and then disposal, any of the devices 100, 500, and 600, and elements thereof may be refurbished for reuse. Refurbishment of the device may include steps such as inspecting the device, removing foreign particles, stains, or odors by washing one or more surfaces of the device, repairing tears or damage to the device, refilling the cushioned portions with additional filler material or replacing the foam, repairing or supplementing the stitching, such as at the seams, replacing any elements or components, replacing missing items from a kit of cushioned support devices, etc. Refurbishing may include decontaminating any of the devices such as by sterilization means, such as the use of gamma radiation, electron-beam radiation, X-ray radiation, Ethylene oxide (EtO), steam, such as through the use of an autoclave, or any combination thereof. And, refurbishing may include repackaging any of the devices and elements thereof The foregoing description of embodiments has been presented for purposes of illustration and description. It is not intended to be exhaustive or to limit the disclosure to the precise form disclosed. Modifications and variations are possible in light of the above teachings or may be acquired from this disclosure. The embodiments were chosen and described in order to explain the principles of the disclosure and its practical application to enable one skilled in the art to utilize the various embodiments and with various modifications as are suited to the particular use contemplated. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited in the claims. For example, elements shown as integrally formed may be constructed of multiple parts or elements, the position of elements may be reversed or otherwise varied, and the nature or number of discrete elements or positions may be altered or varied. The order or sequence of any process or method steps may be varied or re-sequenced according to alternative embodiments. Other substitutions, modifications, changes, and omissions may be made in the design, operating conditions, and arrangement of the embodiments without departing from the scope of the present disclosure.

It is understood that the disclosure may be embodied in other specific forms without departing from the spirit or central characteristics thereof. The present examples and embodiments, therefore, are to be considered in all respects as illustrative and not restrictive, and the invention is not to be limited to the details given herein. The terms "first," "second," "top," "bottom," "left," "right," "proximal," "distal," etc., as used herein, are intended for illustrative purposes only and do not limit the embodiments in any way. It should be noted that the orientation of various elements may differ according to other preferred embodiments and that such variations are intended to be encompassed by the present disclosure. Accordingly, while specific embodiments have been illustrated and described, numerous modifications come to mind without significantly departing from the spirit of the disclosure.

For the purpose of this disclosure, the term "coupled" means the joining of two members directly or indirectly to one another. Such joining may be stationary or moveable in nature. Such joining may be achieved with the two members or the two members and any additional intermediate members being integrally formed as a single unitary body with one another, or with the two members or the two members and any additional intermediate members being attached to one another. Such joining may be permanent in nature or may be removable or releasable in nature.

What is claimed is:

1. A cushioned support device, comprising:
   a pad for supporting a portion of a patient's leg, wherein the pad comprises a top surface, an intermediate surface, two separately constructed pontoons configured to extend parallel to the patient's leg, and a bottom surface, wherein a top pillow is formed of filling material inserted between the top surface and the intermediate surface, and wherein the two separately constructed pontoons are formed by connecting the bottom surface to the intermediate surface;
   wherein the top surface comprises a first material extending along lateral sides of the top pillow and a second material, different from the first material, covering a center portion of the top pillow, the second material configured to conform to the patient's leg;
   a securing system coupled to the pad and configured to secure the portion of the patient's leg to the pad; and
   a connecting member coupled to the pad and configured to couple the cushioned support device to a second cushioned support device.

2. The cushioned support device of claim 1, further comprising an attachment mechanism coupled to the pad and configured to couple the cushioned support device to an object to maintain the cushioned support device on a supporting surface.

3. The cushioned support device of claim 2, wherein the attachment mechanism is configured to removably couple the cushioned support device to the object.

4. The cushioned support device of claim 2, wherein the object is a rail associated with an operating room table.

5. The cushioned support device of claim 1, wherein the deformable material of the center portion is spandex.

6. The cushioned support device of claim 1, wherein the securing system comprises a leg wrap having a first flap configured to removably attach to a second flap.

7. The cushioned support device of claim 1, wherein the connecting member is configured to releasably couple the cushioned support device to the second cushioned support device.

8. The cushioned support device of claim 7 wherein the connecting member comprises a first portion of a buckle clip configured to removably couple with a second portion of the buckle clip on the second cushioned support device.

9. The cushioned support device of claim 1, wherein at least one surface of the pad includes a non-woven material.

10. A kit for supporting a portion of patient anatomy, comprising:
    a first cushioned support device; and
    a second cushioned support device;
    wherein each cushioned support device comprises:
      a pad for supporting a portion of a patient's leg, wherein the pad comprises a top surface, an intermediate surface, two separately constructed pontoons configured to extend parallel to the patient's leg, and a bottom surface, wherein a top pillow is formed of filling material inserted between the top surface and the intermediate surface, and wherein the two separately constructed pontoons are formed by connecting the bottom surface to the intermediate surface;
      wherein the top surface comprises a first material extending along lateral sides of the top pillow and a second material, different from the first material, covering a center portion of the top pillow, the second material configured to conform to the patient's leg;

a securing system coupled to the pad and configured to secure the portion of the patient's leg to the pad; and a connecting member coupled to the pad and configured to couple the cushioned support device to a second cushioned support device.

11. The kit of claim 10, further comprising a knee support pillow.

12. The kit of claim 10, wherein at least one of the cushioned support devices further comprises an attachment mechanism coupled to the pad and configured to couple the cushioned support device to an object to maintain the cushioned support device on a supporting surface.

13. The kit of claim 12, wherein the attachment mechanism is configured to removably couple the cushioned support device to the object.

14. The kit of claim 10, wherein the connecting member of each cushioned support device is configured to removably couple the cushioned support device to the other cushioned support device.

15. The kit of claim 10, wherein the securing system comprises a first flap configured to removably attach to a second flap.

16. A method of refurbishing a cushioned support device, comprising:

providing a cushioned support device for refurbishment, the cushioned support device comprising:

a pad for supporting a portion of a patient's leg, wherein the pad comprises a top surface, an intermediate surface, two separately constructed pontoons configured to extend parallel to the patient's leg, and a bottom surface, wherein a top pillow is formed of filling material inserted between the top surface and the intermediate surface, and wherein the two separately constructed pontoons are formed by connecting the bottom surface to the intermediate surface;

wherein the top surface comprises a first material extending along lateral sides of the top pillow and a second material, different from the first material, covering a center portion of the top pillow, the second material configured to conform to the patient's leg;

a securing system coupled to the pad and configured to secure the portion of the patient's leg to the pad; and a connecting member coupled to the pad and configured to couple the cushioned support device to a second cushioned support device;

inspecting the cushioned support device; and preparing the cushioned support device for re-use.

17. The method of claim 16, further comprising cleaning the cushioned support device.

18. The method of claim 16, further comprising repairing damage sustained by the cushioned support device.

19. The method of claim 16, further comprising filling the pad with a filling material.

* * * * *